(12) United States Patent
McLaughlin et al.

(10) Patent No.: US 8,914,312 B2
(45) Date of Patent: Dec. 16, 2014

(54) METHOD OF CONTAMINANT PREDICTION

(75) Inventors: Michael John McLaughlin, Fullarton (AU); Sean Thomas Forrester, Richmond (AU); Leslie Joseph Janik, McLaren Flat (AU)

(73) Assignee: Commonwealth Scientific and Industrial Research Organisation, Australian Capital Territory (AU)

(\*) Notice: Subject to any disclaimer, the term of this patent is extended or adjusted under 35 U.S.C. 154(b) by 31 days.

(21) Appl. No.: 13/497,145

(22) PCT Filed: Sep. 24, 2010

(86) PCT No.: PCT/AU2010/001261
§ 371 (c)(1),
(2), (4) Date: May 24, 2012

(87) PCT Pub. No.: WO2011/035391
PCT Pub. Date: Mar. 31, 2011

(65) Prior Publication Data
US 2012/0226653 A1  Sep. 6, 2012

Related U.S. Application Data

(60) Provisional application No. 61/245,346, filed on Sep. 24, 2009.

(51) Int. Cl.
*G06F 15/18* (2006.01)
*G01N 21/35* (2014.01)
*G01N 33/24* (2006.01)

(52) U.S. Cl.
CPC .......... *G01N 21/359* (2013.01); *G01N 21/3563* (2013.01); *G01N 33/241* (2013.01)
USPC .......................................................... 706/12

(58) Field of Classification Search
USPC .......................................................... 706/52
See application file for complete search history.

(56) References Cited

U.S. PATENT DOCUMENTS 5,191,786 A * 3/1993 Baughman et al. .......... 73/64.45
2001/0025232 A1 * 9/2001 Klimasauskas et al. ........ 703/13
(Continued)

FOREIGN PATENT DOCUMENTS

WO   WO 2009/080049 A1   7/2009

OTHER PUBLICATIONS

Vreugdenhil, Andrew J. and Ian S. Bulter. "Detection of the ENgine Anti-knock Additive Methycyclopentadienyl Manganese Tricarbonyl (MMT) from Unleaded Gasoline in Soil by Diffuse Reflectance Infrared Fourier Transform Spectroscopyand Mass SPectrometry" Applied Spectroscopy, vol. 49, Issue 4, pp. 482-485 1995 [ONLINE] Downloaded Apr. 1, 2014 http://www.*

(Continued)

*Primary Examiner* — Ben Rifkin
(74) *Attorney, Agent, or Firm* — Nixon & Vanderhye P.C.

(57) ABSTRACT

Method of selectively predicting hydrocarbon concentration in a sample of unknown hydrocarbon concentration, by (i) separately subjecting two or more samples of known hydrocarbon concentration to infrared (IR) radiation, (ii) separately detecting an IR signal from the samples of known hydrocarbon concentration, (iii) analyzing the IR signals using a multivariate chemometric technique to produce a training data set, (iv) generating a predictive model for hydrocarbon concentration based on the training data set, (v) subjecting the unknown sample to infrared (IR) radiation, (vi) detecting an IR signal from the unknown sample, (vii) applying the predictive model to the IR signal from the unknown sample. Thereafter, as step (viii), hydrocarbon concentration in the unknown sample is selectively predicted.

15 Claims, 14 Drawing Sheets

(56) References Cited

U.S. PATENT DOCUMENTS

2003/0227382 A1* 12/2003 Breed .................. 340/539.13
2010/0015714 A1* 1/2010 Saini et al. .................. 436/25

OTHER PUBLICATIONS

Schwartz, Marietta "Interpretation of Infrared Spectra" 2008 [ONLINE] Downloaded Apr. 1, 2014 http://ocw.umb.edu/chemistry/organic-chemistry-i-lecture/lecture-links/notes92208.pdf.*

Kardamakis, et al; "Linear predictive spectral coding and independent component analysis in identifying gasoline constituents using infrared spectroscopy"; *Chemometrics and Intelligent Laboratory Systems*, vol. 89, pp. 51-58 May 26, 2007.

Balabin, et al; "Comparison of linear and nonlinear calibration models based on near infrared (NIR) spectroscopy data for gasoline properties predictions"; *Chemometrics and Intelligent Laboratory Systems*, vol. 88, pp. 183-188, May 5, 2007.

Janik, L.J., et al; "The prediction of soil chemical and physical properties from mid-infrared spectroscopy and combined partial least-squares regression and neural networks (PLS-NN) analysis"; *Chemometrics and Intelligent Laboratory Systems*, vol. 97, pp. 179-188 (2009).

Hazel, G., et al; "Multivariate Analysis of Mid-IR FT-IR Spectra of Hydrocarbon-Contaminated Wet Soils"; *Applied Spectroscoy*, vol. 51, No. 7, pp. 984-989 (1997).

Grabiec-Raczak, E., et al; "Determination of Oil in Environmental Samples Using FTIR Spectrometry Technique"; *ECOpole'05, Ksiega Konferencjna/Proceedings*, 14$^{th}$, pp. 85-89, Oct. 20-22, (2005).

* cited by examiner

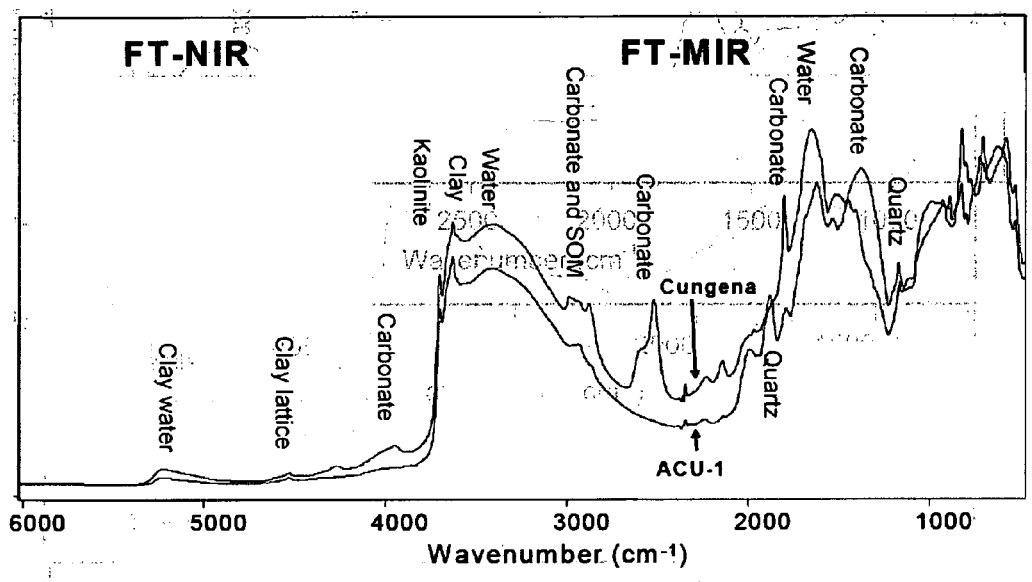
Figure 4
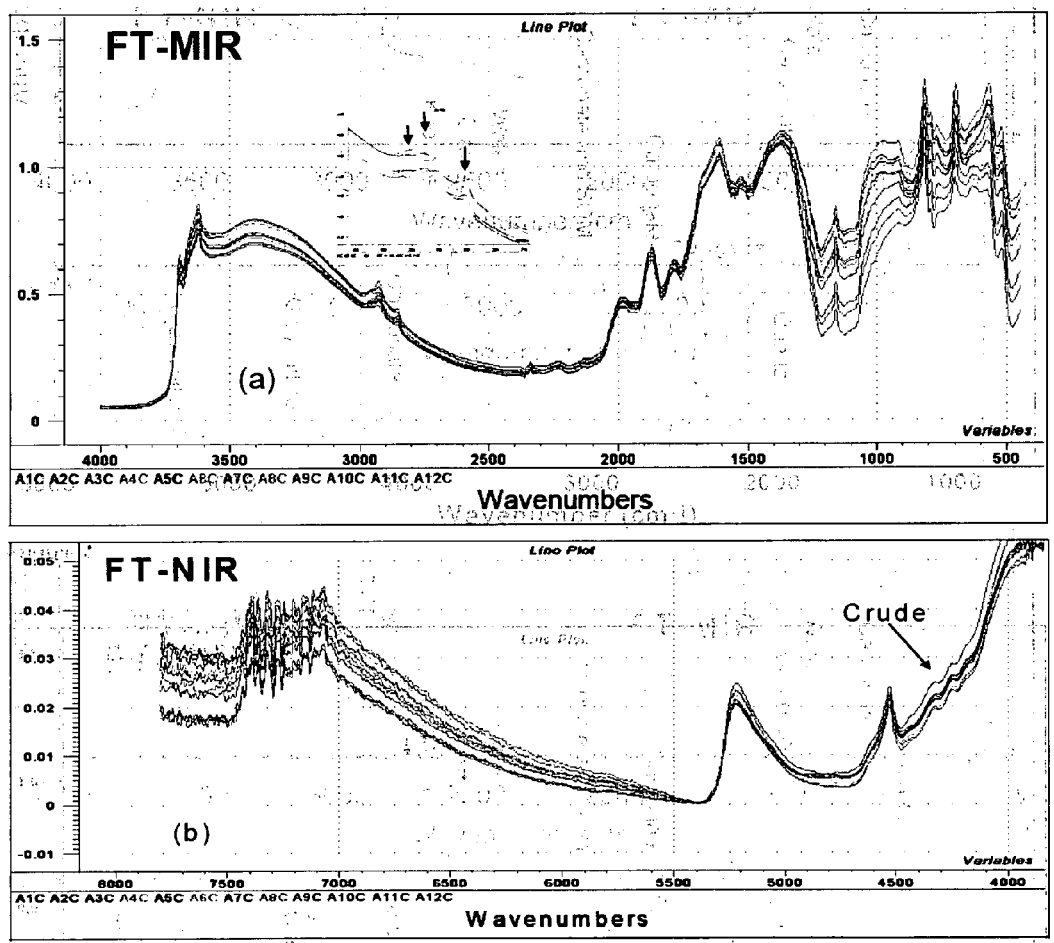
Figure 5 (a) and (b)

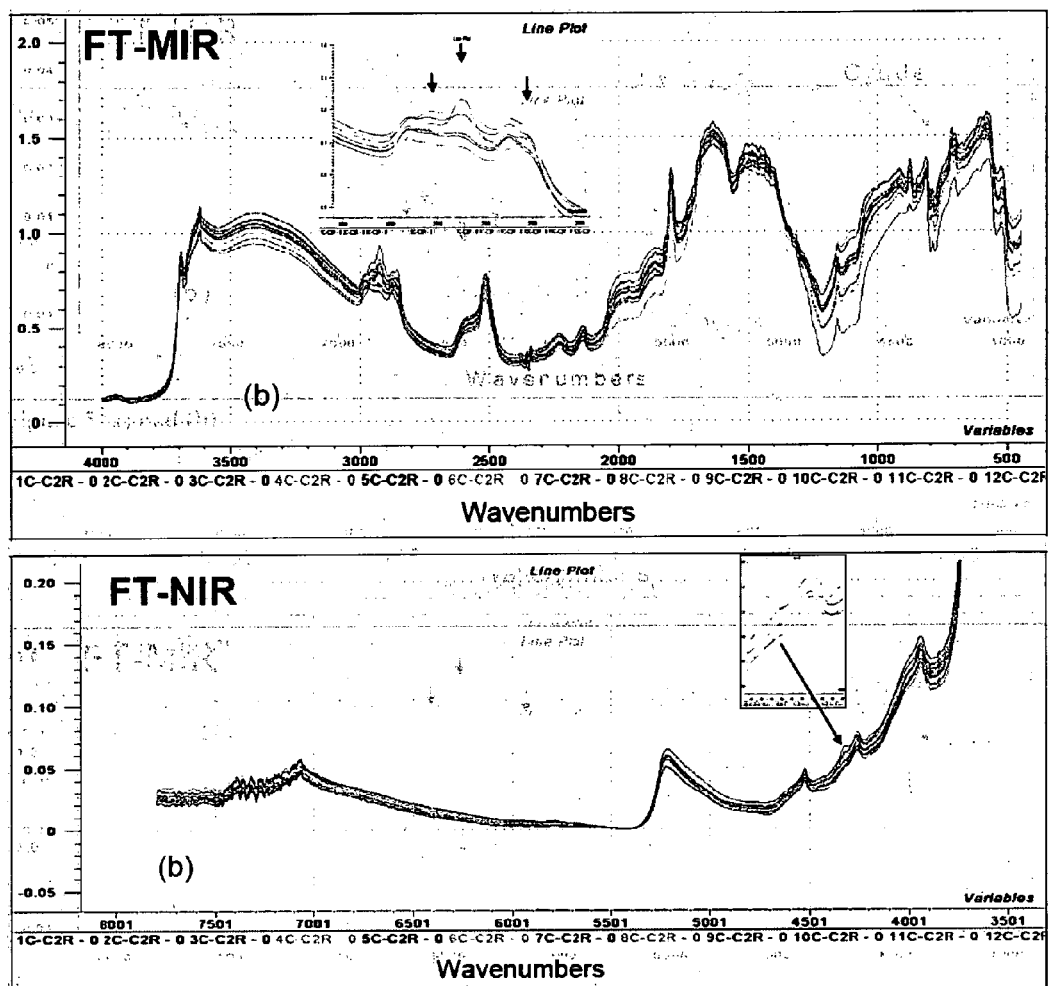
Figure 6 (a) and (b)

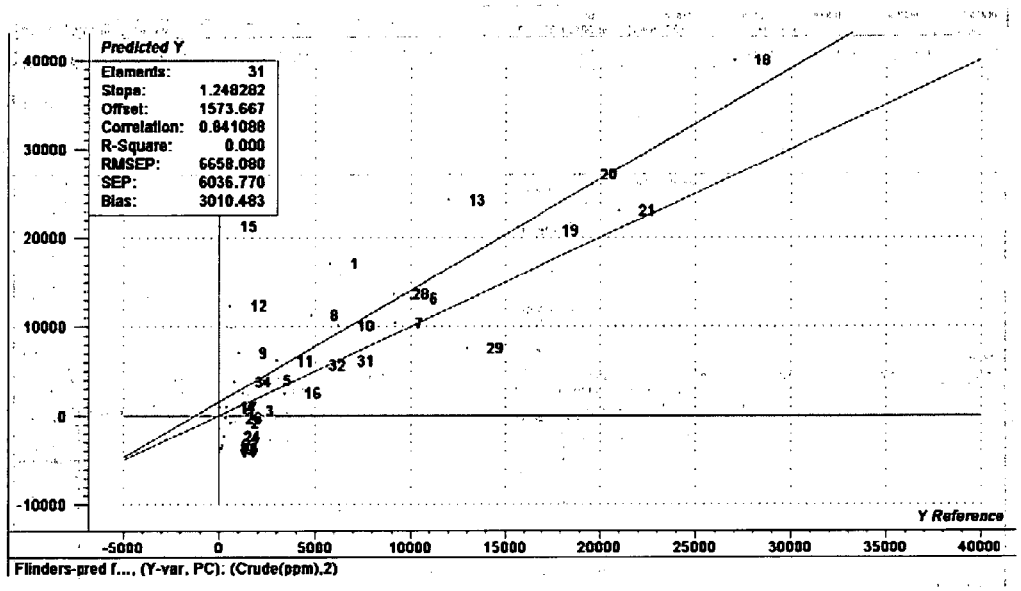
Figure 14
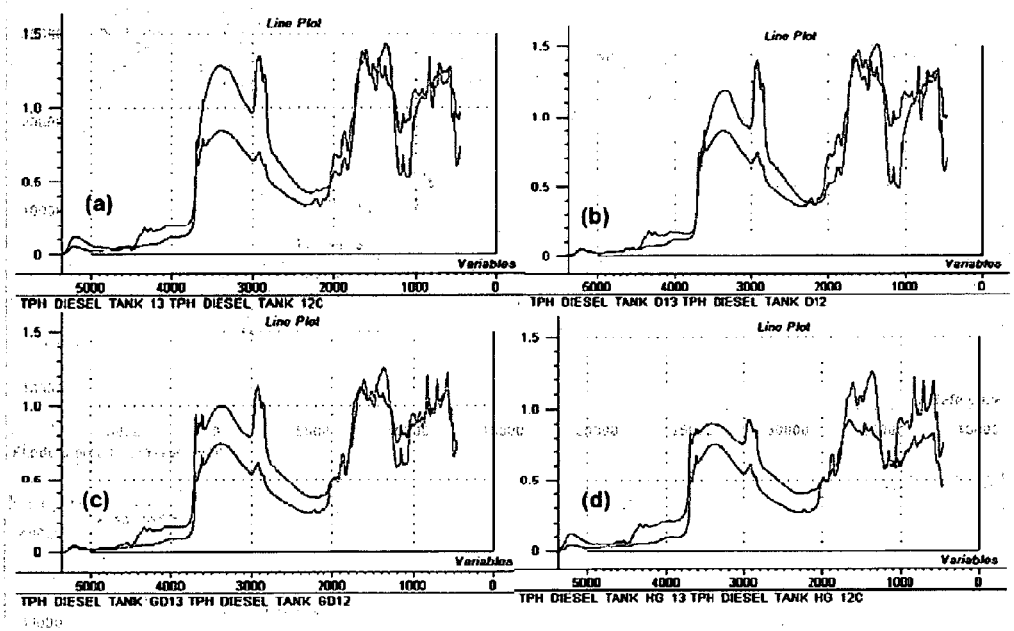
Figure 15 (a), (b), (c) and (d)

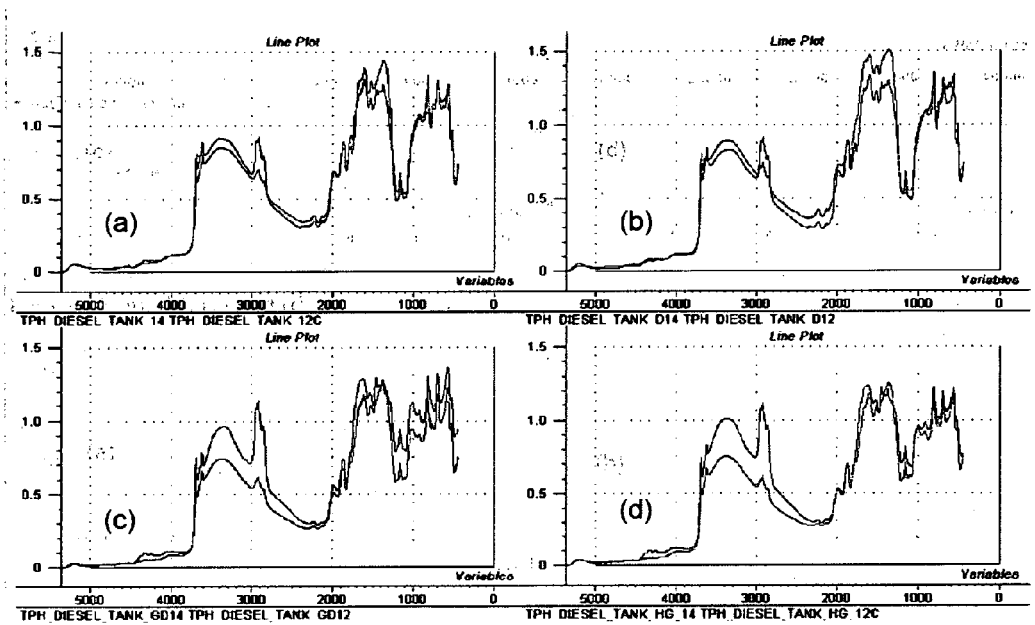
Figure 16 (a), (b), (c) and (d)
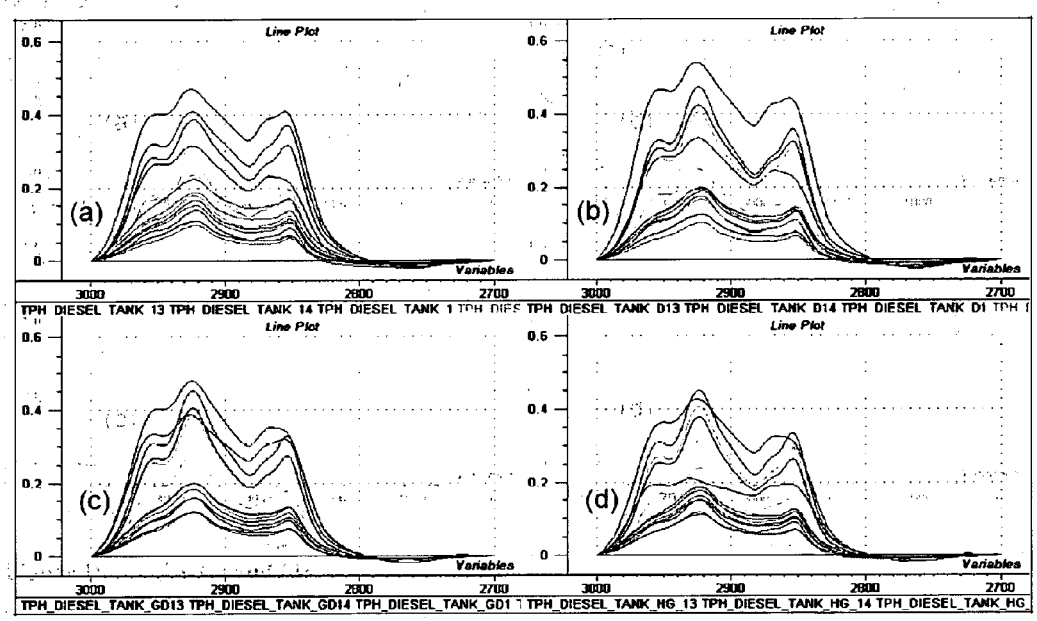
Figure 17 (a), (b), (c) and (d)

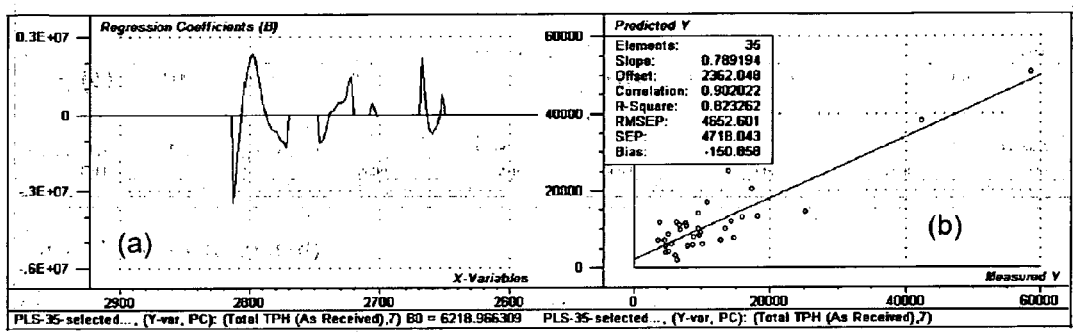
Figure 18 (a) and (b)

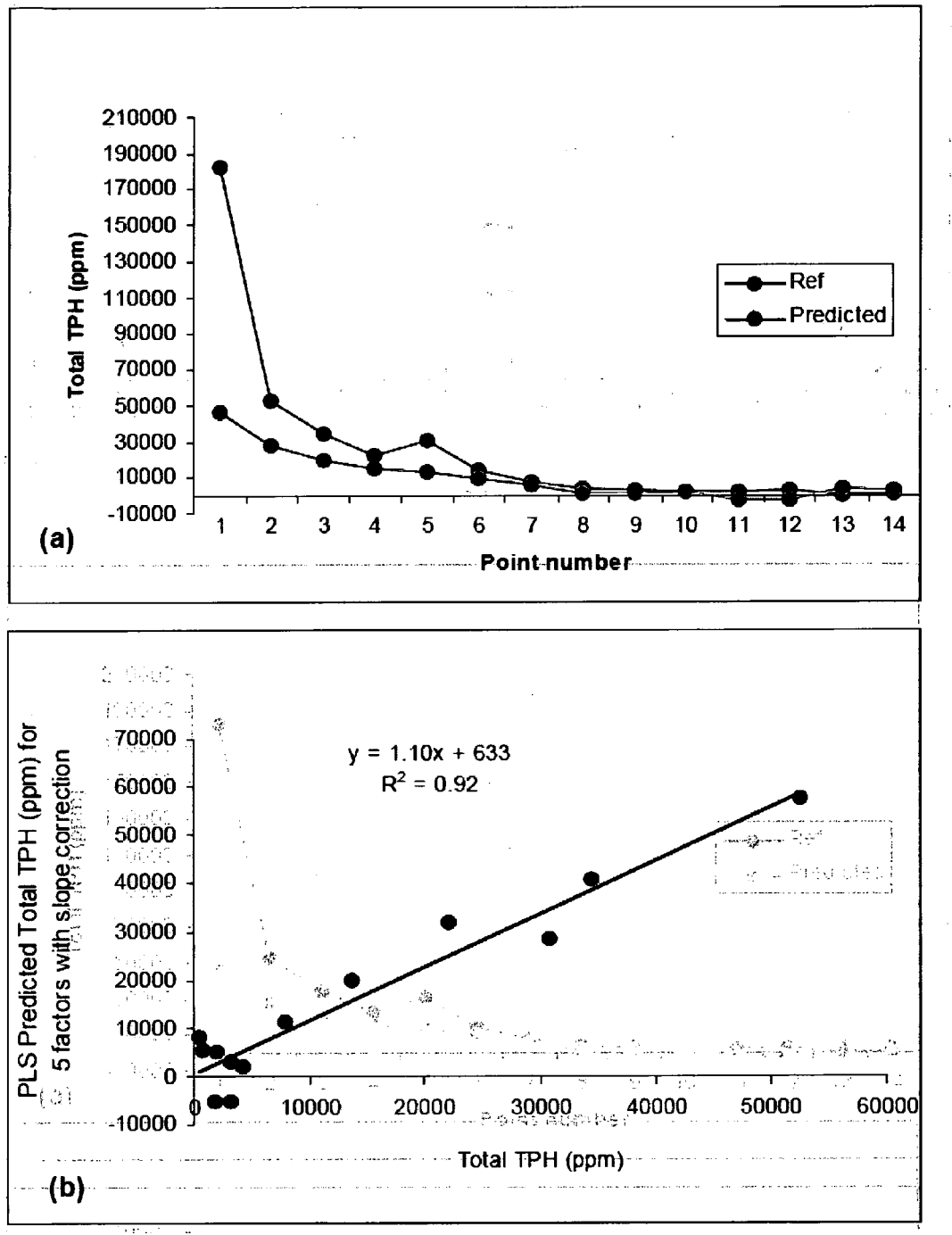
Figure 19 (a) and (b)

METHOD OF CONTAMINANT PREDICTION

This application is the U.S. national phase of International Application No. PCT/AU2010/001261 filed 24 Sep. 2010 which designated the U.S. and claims priority to U.S. Provisional Application No. 61/245,346 filed 24 Sep. 2009, the entire contents of each of which are hereby incorporated by reference.

FIELD

The present invention relates to methods for the prediction of hydrocarbon, in particular total petroleum hydrocarbons (TPH), in an environmental sample using infrared (IR) detection of samples of known hydrocarbon concentration to generate a partial least squares (PLS) hydrocarbon prediction model. The method is capable of utilising IR spectrometry data taken directly from an environmental sample (such as a soil, sediment, silt, rock or mineral sample) to predict hydrocarbon concentration in the sample.

BACKGROUND

Most petroleum hydrocarbon substances are derived from crude oil and, typically, comprise a mixture of short and medium length hydrocarbon compounds. The less volatile components of petroleum hydrocarbons can become environmental contaminants; they may remain in the environment for extended periods and become toxic to wildlife, flora and/or humans. Such contaminations are usually difficult, if not impossible, to observe unless gross contamination has occurred. Therefore, methods for the rapid and/or simple prediction of petroleum hydrocarbons in the environment (i.e. as may be found in soils, sludges and waterways) are desirable for monitoring environmental contamination and/or assessing a site.

For instance, with high urban growth, city fringes are gradually encroaching on areas that were formerly disused and/or predominantly industrial in nature. These sites present usable and valuable property for the further growth and development of many industrialised cities. However, many such sites have been contaminated by petroleum hydrocarbon leakage from their previous industrial uses, and some have been exposed to these materials time and time again. While these sites hold great potential, the environmental protection guidelines of most industrialised countries set safety standards for the minimum acceptable concentration of petroleum hydrocarbons in soils or other environmental matrices. Thus, to be placed in order for non-industrial reuse (e.g. residential or light-industrial uses), the amount of petroleum hydrocarbon on these sites must be reduced to acceptable levels for their intended future use. While many options are available for the treatment of contaminated sites, a significant portion of the time and costs involved in treating these sites is consumed in the monitoring of petroleum hydrocarbon over time. This is particularly true of the more sustainable remediation treatment techniques, as on site and/or real time techniques are not currently available for petroleum hydrocarbon monitoring.

In addition, causing an environmental contamination event can be considered as a serious offence with hefty penalties applicable to entities that flagrantly cause serious contamination. In these instances, regulators must rely on time-intensive and costly techniques to monitor the contamination event, with the delay in testing time, in turn, causing further delay in possible action to control the severity of the event.

Such testing situations typically involve the testing of numerous soil samples involving the extraction and quantitation of contaminant components, which is generally time consuming and labour intensive. For example, for the analysis of total petroleum hydrocarbons (TPHs) in soil, testing is usually carried out via supercritical fluid extraction of the TPH components from the soil samples followed by the quantitative analysis of the TPH either by gas chromatography-flame ionisation detection (GC-FID) and/or gas chromatography-mass spectrometry (GC-MS). GC-MS is particularly suitable for the quantitative analysis of the more volatile components of TPHs (i.e. compounds in the C6 to C10 carbon chain range), but often utilises a purge and trap method where a heated purge gas is used to introduce the TPH components to the GC column; a procedure that, alone, may take up to twenty minutes per sample. For the less volatile components of TPH (i.e. compounds in the C10 to C36 range), detection in soil or sediment samples can potentially be achieved by the direct extraction of the contaminants using a solvent such as methylene chloride, following sample sonication, and introduction of the TPH components to a GC column for GC-MS analysis or analysis by Fourier Transform (FT) IR reflectance (Sadler and Connell, 2003). However, these techniques, although they potentially provide accurate results, can also be time consuming and labour intensive. Moreover, none of these methods, which necessarily involve the use of sensitive equipment, are suited to on-site analysis of contaminants such as hydrocarbons.

Accordingly, a rapid and/or simple method for predicting the concentration of hydrocarbon contaminants, and particularly TPH components, in a site could provide significant cost advantages (i.e. in terms of reduced testing costs and/or the avoidance of delays in test results leading to productivity losses) and/or other advantages of rapid response, such as the capacity to undertake preventative measures to prevent further contamination and/or to limit contaminant spread.

Infrared (IR) spectroscopic techniques offer a possible alternative approach to supercritical fluid extraction and gas chromatography analyses of site contaminants. IR spectrometry distinguishes between chemical compounds by detecting the selective absorption of different IR wavelengths by vibrating chemical bonds; thus, each compound present in a sample being analysed that is IR active has a unique IR "spectral signature" enabling its identification and quantitation. However, while IR spectrometry-based techniques, such as diffuse reflectance infrared fourier transform (DRIFT) spectroscopy with partial least-squares (PLS) chemometrics (with mid-infrared (MIR) and near-infrared (NIR); Janik and Skjemstad, 1995; Reeves et al., 1999; and Cozzolino and Moron, 2003), have been employed in agricultural soil analysis for the detection of a large number of soil properties such as, for example, organic carbon, exchangeable cations, air-dry moisture and clay content, they have not to-date been used for the qualitative or quantitative analysis of contaminants such as petroleum hydrocarbon in complex mixtures such as soil, sediment, rock or mineral samples. The spectral peaks typically attributable to petroleum hydrocarbon contaminants may also occur in frequency regions due to the presence of naturally-occurring organic matter (NOM) and/or be masked by other factors. For example, using DRIFT, where the radiation penetrates a short distance (a few tens of micrometers) into soil, quartz (as sand) and clays can give particularly strong MIR spectral signatures which can, as a result, overlap with peaks potentially useful for TPH determination.

The present invention is directed at IR spectrometry-based methods for predicting hydrocarbon contaminants in an environmental sample, particularly a soil, sediment, rock, mineral or other solid sample, which may overcome one or more of the problems associated with the prior art.

SUMMARY

In a first aspect, the present invention provides a method of selectively predicting hydrocarbon concentration in a sample of unknown hydrocarbon concentration (the unknown sample), said method comprising the steps of:
  (i) separately subjecting two or more samples of known hydrocarbon concentration to infrared (IR) radiation, at least two of the samples having different hydrocarbon concentrations;
  (ii) separately detecting an IR signal from the samples of known hydrocarbon concentration;
  (iii) analysing the IR signals using a multivariate chemometric technique to produce a training data set;
  (iv) generating a predictive model for hydrocarbon concentration based on the training data set;
  (v) subjecting the unknown sample to infrared (IR) radiation;
  (vi) detecting an IR signal from the unknown sample;
  (vii) applying the predictive model to the IR signal from the unknown sample; and thereafter
  (viii) selectively predicting hydrocarbon concentration in the unknown sample.

In a second aspect, the present invention provides a method for generating a model to selectively predict hydrocarbon concentration in a sample of unknown hydrocarbon concentration (the unknown sample), said method comprising the steps of:
  (i) separately subjecting two or more samples of known hydrocarbon concentration to infrared (IR) radiation, at least two of the samples having different hydrocarbon concentrations;
  (ii) separately detecting an IR signal from the samples of known hydrocarbon concentration;
  (iii) analysing the IR signals using a multivariate chemometric technique to produce a training data set;
  (iv) generating a predictive model for hydrocarbon concentration based on the training data set;
  (v) separately subjecting one or more further sample(s) of known hydrocarbon concentration to infrared (IR) radiation;
  (vi) separately detecting an IR signal from the further sample(s) of known hydrocarbon concentration; and thereafter
  (vii) calibrating the predictive model using the IR signal of the further sample(s) of known hydrocarbon concentration;
wherein application of the predictive model to the unknown sample selectively predicts hydrocarbon concentration therein.

In a third aspect, the present invention provides a software program for selectively predicting hydrocarbon concentration from inputted IR signal data of an unknown sample, wherein said program performs a calculation comprising:
  (i) generating a predictive model for hydrocarbon concentration by applying a multivariate chemometric technique to inputted IR signal data from two or more samples of known hydrocarbon concentration wherein at least two of the samples have different hydrocarbon concentrations to produce a training data set, and calibrating the predictive model using inputted IR signal data of one or more further sample(s) of known hydrocarbon concentration; and thereafter
  (ii) applying the predictive model to the inputted IR signal data of the unknown sample to provide a selective prediction of hydrocarbon concentration.

BRIEF DESCRIPTION OF THE FIGURES

FIG. 4 shows the FTIR spectra of two reference soils, "Ref A" and "Ref B", and designation of their major peaks;

FIG. 5 shows the FTIR spectra of Ref A soil spiked with 0-90,000 ppm crude oil, (a) FT-MIR spectra, and (b) FT-NIR spectra. Crude oil alkyl peaks are indicated in the inset in (a) and also in (b);

FIG. 6 shows the FTIR spectra of Ref B soil spiked with 0-90,000 ppm crude oil, (a) FT-MIR spectra, and (b) FT-NIR spectra. Crude oil alkyl peaks are indicated in the inset in (a) near 2950 to-2850 $cm^{-1}$ and in (b) at 4320 $cm^{-1}$;

FIG. 14 shows the PLS prediction of Site A soils from the Ref B calibration model;

FIG. 15 shows the FT-MIR spectra of the "Farm A" samples at intervals from the source of contamination wherein the sample closest to the diesel tank is depicted as sample 13, and the sample furthest from the tank is depicted as sample 12, and wherein samples are scanned (a) as received, (b) air-dried, (c) air-dried and ground, and (d) air-dried, ground and heated to 40° C.;

FIG. 16 shows the FT-MIR spectra of the Farm A samples at intervals from the source of contamination wherein the second closest to the diesel tank is depicted as sample 14, and the sample furthest from the tank is depicted as sample 12, and wherein the samples are scanned (a) as received, (b) air-dried, (c) air-dried and ground, and (d) air-dried, ground and heated to 40° C.;

FIG. 17 shows the FT-MIR spectra of all the Farm A samples at intervals from the source of contamination scanned in the 3000 $cm^{-1}$ to 2700 $cm^{-1}$ spectral region, and wherein the samples are scanned (a) as received, (b) air-dried, (c) air-dried and ground, and (d) air-dried, ground and heated to 40° C.;

FIG. 18 (a) shows the PLS regression coefficients for the first seven PLS factors in the 2800 cm$^{-1}$ to 2600 cm$^{-1}$ spectral region, and (b) shows the FT-MIR PLS calibration for total TPH derived from 35 Site B samples;

FIG. 19 (a) shows the PLS regression predicted and reference total TPH of samples at 10 cm intervals from the tank source wherein the final samples is an unaffected point, and (b) PLS regression predicted versus reference total TPH concentrations using five PLS factors and slope correction;

DETAILED DESCRIPTION

Figure 1A:
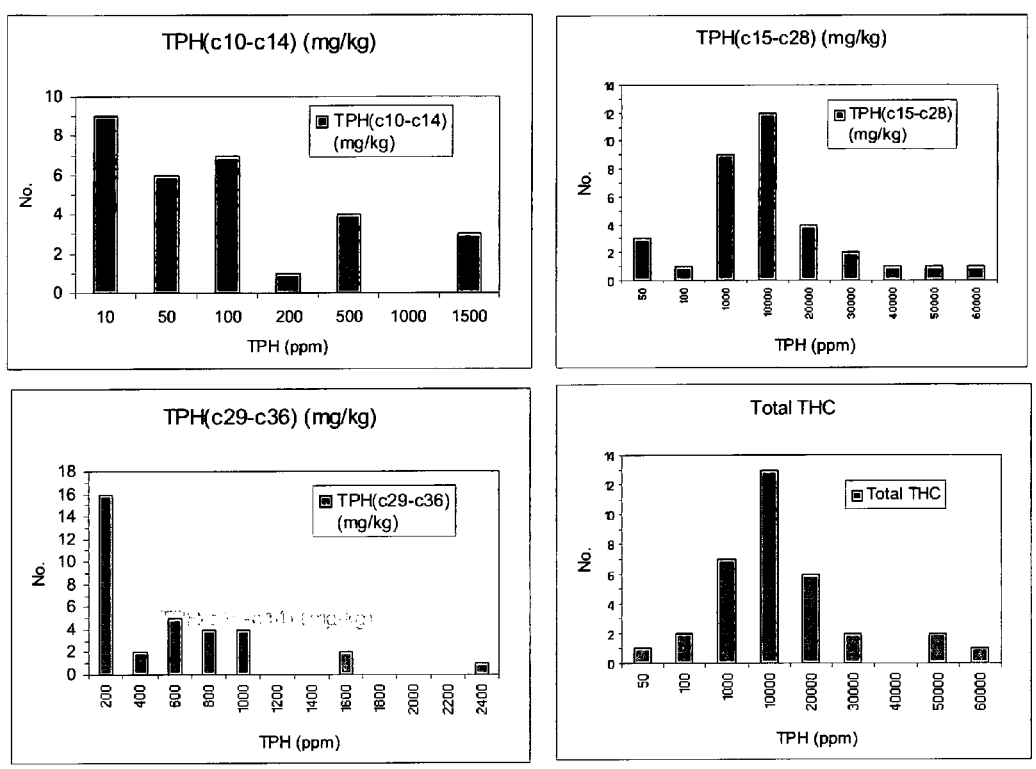
FIG. 1 provides a histogram showing the distribution of petroleum hydrocarbons (C10 to C14, C15 to C28, C29 to C36 and total TPH) in "real" contaminated soils; the "Site A" soils are shown at (a) and the "Site B" soils are shown at (b)
Figure 1:
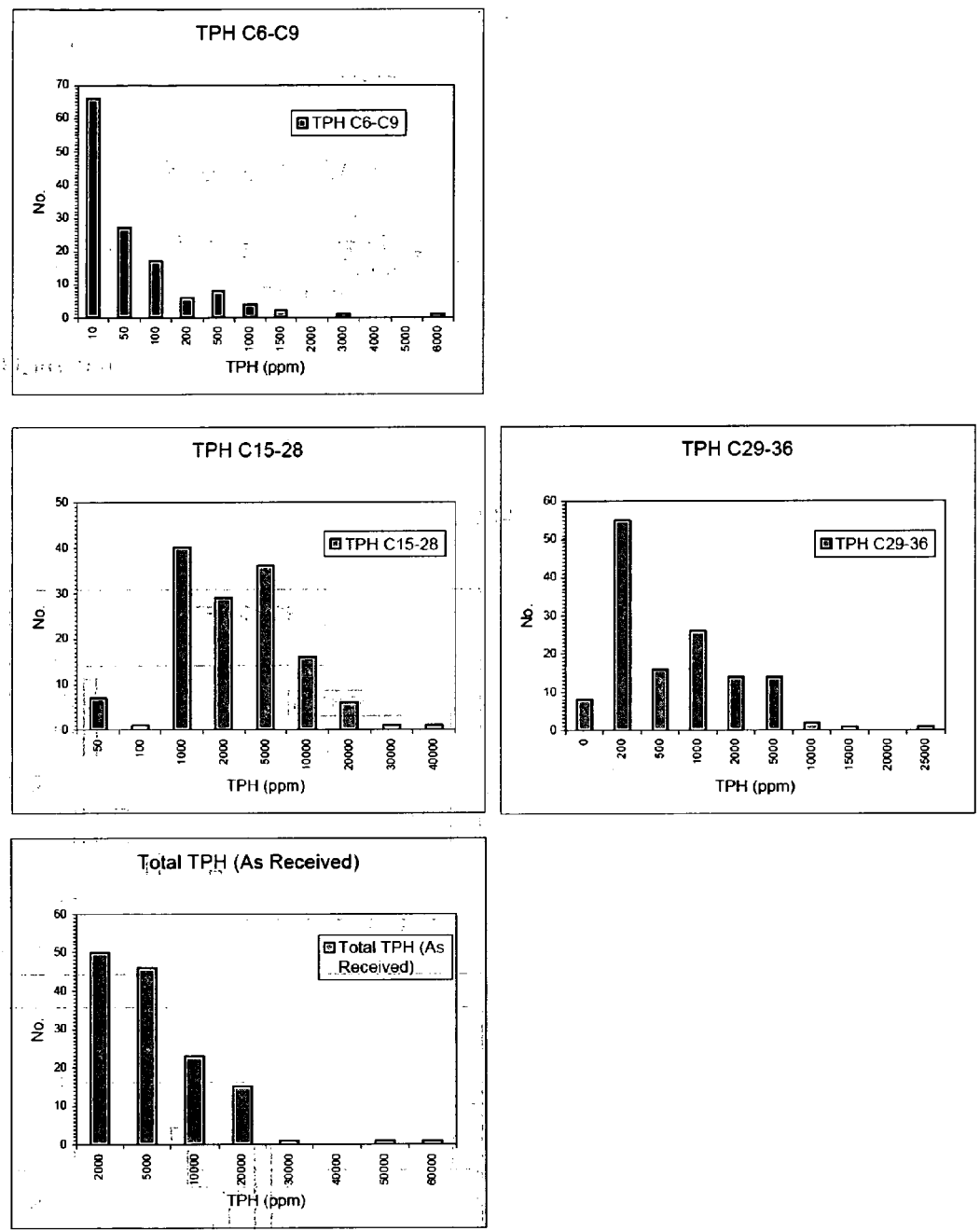

Present methods for the determination of hydrocarbon concentration in an environmental sample, such as a soil, sediment, rock, mineral or other solid sample, requires the partial or complete extraction of the hydrocarbon compounds from the sample, which can be time consuming and labour intensive. Further, analyses using current methods cannot selectively distinguish specific types of hydrocarbons. For instance, current techniques cannot be use to selectively distinguish TPHs from hydrocarbons derived from NOM which may, for example, give an overestimation of toxicity risk and/or an underestimation of the effectiveness of remediation following contamination events and/or a false identification of the presence of petroleum hydrocarbons during exploration. It is therefore desirable that alternative methods be developed which allow for the selective prediction of hydrocarbon directly from an environmental sample (i.e. such that extraction steps are avoided).

In the case of petroleum hydrocarbon prediction, it has, previously, been widely accepted that the typical presence of mineral components and other naturally-occurring materials such as NOM would mask or hide characteristic signals of TPH components that might otherwise be useful for the prediction of the presence or concentration of petroleum hydrocarbons. The present applicant has, however, identified a method for generating a multivariate chemometric hydrocarbon prediction model based on infrared (IR) detection that overcomes the spectral effects of other environmental materials. This model is capable of utilising IR spectrometry data taken directly from an environmental sample to selectively predict hydrocarbon concentration.

Thus, in a first aspect the present invention provides a method of selectively predicting hydrocarbon concentration in a sample of unknown hydrocarbon concentration (the unknown sample), said method comprising the steps of:
  (i) separately subjecting two or more samples of known hydrocarbon concentration to infrared (IR) radiation, at least two of the samples having different hydrocarbon concentration;
  (ii) separately detecting an IR signal from the samples of known hydrocarbon concentration;
  (iii) analysing the IR signals using a multivariate chemometric technique to produce a training data set;
  (iv) generating a predictive model for hydrocarbon concentration based on the training data set;
  (v) subjecting the unknown sample to infrared (IR) radiation;
  (vi) detecting an IR signal from the unknown sample;
  (vii) applying the predictive model to the IR signal from the unknown sample; and thereafter
  (viii) selectively predicting hydrocarbon concentration in the unknown sample.

The selective prediction of hydrocarbon concentration may comprise the prediction of total hydrocarbon concentration (e.g. for the determination of total recoverable hydrocarbon) or the prediction of a selected type or group of hydrocarbon compounds. In particular, the method of the first aspect may be utilised to selectively predict petroleum hydrocarbon concentration or to selectively predict the concentration of hydrocarbon derived from NOM. NOM predictions may be particularly advantageous, for instance, in monitoring the degradation of NOM (e.g. during composting processes) or in petroleum exploration (e.g. to either locate significant reservoirs of NOM or NOM derived compounds, to make a determination of NOM to TPH ratio, or to selectively exclude NOM concentration from TPH predictions).

It will be understood by persons skilled in the art that the methods described herein may be applied to the selective prediction of types or groups of hydrocarbons that may not be specifically mentioned. Such modifications may be made by making appropriate selections, modifications, adjustments and/or optimisations of IR signal or IR signal data to select for the desired groups of compounds. The necessary selections, modifications, adjustments, and/or optimisations may be appreciated with reference to the methods for the selective prediction of petroleum hydrocarbon.

Thus, the method of the first aspect preferably provides a method of selectively predicting petroleum hydrocarbon concentration in a sample of unknown petroleum hydrocarbon concentration, wherein step (viii) comprises selectively predicting petroleum hydrocarbon concentration in the unknown sample.

The term "hydrocarbon" as used herein in relation of an environmental sample is to be understood to mean one or more hydrocarbon compounds. In the present context, hydrocarbons can include plant and/or mineral derived hydrocarbons. Mineral derived hydrocarbons include petroleum hydrocarbons. The term "petroleum hydrocarbon" as used herein in relation to an environmental sample is to be understood to refer to substances comprising one or more hydrocarbon compounds considered to form a component of the group known as "total petroleum hydrocarbon" (TPH). Such substances include crude oil or substances derived from crude oil (e.g. petroleum products) and, typically, comprise C6 to C36 hydrocarbon compounds including a —CH$_3$ (methyl) terminus.

The term "infrared signal" or "IR signal" as used herein in relation to IR radiation or IR spectrometry or spectra, is to be understood to refer to any indicator of absorbance and/or reflection of IR radiation. For example, in IR spectroscopy, an IR signal may comprise an absorbance or reflection peak in the IR spectrum.

As used herein, all wavenumbers are expressed in cm$^{-1}$ units, and spectral intensities as absorbance units (A) wherein A=Log Reflectance$^{-1}$.

Step (i) may be conducted directly on the sample (i.e. without any pre-processing or pre-treatment of the sample), however, for some samples such as soil, sediment, rock, mineral or other solid samples, it may be preferred to crush or grind and/or sieve the sample prior to exposure to the IR radiation, so as to eliminate large particles and/or to ensure substantial uniformity in sample particle sizes. For many solid samples, the surface characteristics of the particles within a sample may contribute to the "spectral definition" of the sample. It has, however, been found that if the sample is subjected to crushing or grinding, there can be a decrease in random baseline absorbance variations as well as reducing sample non-homogeneity. Accordingly, for some samples, the sample may be pre-processed before subjecting it to IR radiation. In some embodiments, the pre-processing produces a sample comprising particles measuring less than 500 μm. In some embodiments, the pre-processing produces a sample comprising particles measuring less than 200 μm. In further embodiments, the pre-processing produces a sample comprising particles measuring less than about 100 μm.

Further, it has been found that on certain particle surfaces, for instance, particles derived from stormwater, sediment, compost products, or organic industrial sludges, the presence of water or other solvents may "mirror" the IR radiation thereby causing distortion and/or the amplification of minor IR signals. Therefore, for some samples, it may be preferred, particularly when IR absorbance spectroscopy is used, to dry the sample prior to subjecting the sample to IR radiation. Drying the sample may be conducted in air at a temperature of less than 40° C. so as to avoid the volatilisation or modification of hydrocarbon. Alternatively, the sample may be freeze dried to remove water or other solvents from the sample prior to subjecting the sample to IR radiation. In some embodiments, the drying of the sample is conducted at ambient temperature.

The method of the present invention may be suitable for the selective prediction of hydrocarbon concentration in a liquid sample, an aqueous sample, a semi-solid sample, a sludge or an emulsion (i.e. without the need to dry the sample to a solid form). This can be achieved by, for example, utilising mirror reflection techniques (i.e. transflectance techniques) to overcome the difficulty of specular reflectance distortions that may otherwise be experienced using DRIFT. Thus, the prediction of petroleum hydrocarbon concentration in materials in wet or damp conditions need not be delayed by the requirement to transport samples off-site for drying.

Moreover, for some samples, it may be preferred to mix in a known amount of a diluent, such as an alkali halide (e.g. KBr) or fine clay, so as to reduce specular distortion of peaks. It has been observed that the IR signal of petroleum hydrocarbon may be reduced by the presence of clay particles in the sample. It is suspected that clays and other porous media reduce pore space and effectively shield the hydrocarbon from the IR radiation (which can only penetrate the sample to a depth of about 5 μm to 20 μm) through the absorption of the petroleum hydrocarbon within the solid particle.

The present methods may find application for hydrocarbon prediction in a range of environmental matrices, for instance, in soil, rock, silt, sediment, stormwater, compost products, organic fertilizers, organic industrial sludges, and semi-solids. Preferably, the use of the present invention is intended for the prediction of petroleum hydrocarbon concentration in an environmental sample such as a soil, rock, mineral, sediment sample, tarry material or oily sludge. Advantageously, the method may be used for hydrocarbon prediction in unground samples, such as in situ samples.

Common solid environmental samples such as soils, silts, sediments and other solid environmental matrices often comprise mineral components or other naturally-occurring materials that may cause interference in performing IR spectrometry for petroleum hydrocarbon. In particular, these materials were previously believed to mask or hide regions of the IR spectrum in which alkyl signals, characteristic signals of hydrocarbon compounds, are known to be located. For example, these materials may give a very strong IR signal that masks or dampens weaker IR signals or otherwise introduces "spectral noise" preventing the differentiation or identification of useful peaks.

For instance, soil minerals can give strong IR signals in regions of the MIR and NIR; for example, strong IR absorption peaks below 2000 $cm^{-1}$, particularly in the region of 1100 $cm^{-1}$ and 1000 $cm^{-1}$, are apparent in soil samples comprising quartz (i.e. sand) and clays due to the presence of silicate ($—SiO_2$) structures in these substances and the consequent Si—O stretching vibration. The presence of other types of NOM bearing carboxylate (COO—) groups or carboxyl (—COOH) groups can be apparent from strong IR signals at 1600 $cm^{-1}$ and 1400 $cm^{-1}$, and near to 1720 $cm^{-1}$, respectively. Also, carbonate ($—CO_3$) groups generate characteristic IR absorption peaks in the regions in and near 2980 $cm^{-1}$ to 2870 $cm^{-1}$, 2600 $cm^{-1}$ to 2500 $cm^{-1}$ and 1810 $cm^{-1}$, with the main $—CO_3$ peak apparent near 1375 $cm^{-1}$. These peaks overlap with several regions, mainly the 2900 $cm^{-1}$ to 2800 $cm^{-1}$ spectral region, where peaks resulting from the presence of alkyl groups (such as $—CH_3$ of petroleum hydrocarbon compounds) may also be found. For example, characteristic IR absorption peaks for alkyl groups are observed in the 2950 $cm^{-1}$ to 2850 $cm^{-1}$ region near 2955 $cm^{-1}$ ($—CH_3$), 2931 $cm^{-1}$ and 2856 $cm^{-1}$ ($—CH_2$) (corresponding overtone peaks for these vibrations can be seen in the NIR at 4388 $cm^{-1}$, 4329 $cm^{-1}$ and 4256 $cm^{-1}$), however due to the potential interference caused by strong IR signals from NOM-derived alkyl groups and/or carbonate groups, it has not been previously considered possible to use one or more peaks in these regions as an indicator of the presence of petroleum hydrocarbon in complex mixtures such as soils.

The methods of the present invention are therefore based upon the surprising finding that multivariate chemometric modelling techniques are capable of discriminating between data that is selectively characteristic of specific types or groups of hydrocarbons, such as petroleum hydrocarbons, and data that is generated from other substances commonly found in environmental samples, in particular data arising from the presence of NOM and carbonate. It is possible to predict the concentration of petroleum hydrocarbon in an environmental sample by applying a multivariate chemometric model predictive of petroleum hydrocarbon, generated from environmental samples of known petroleum hydrocarbon concentration. In many instances, the accuracy of the predictive models described herein are comparable to current standard techniques such as GC techniques with further refinement possible through calibration methods to potentially exceed the accuracy of current standard techniques.

Step (i) of the method of the first aspect comprises separately subjecting two or more samples of known hydrocarbon concentration to infrared (IR) radiation, at least two of the samples having different hydrocarbon concentration. In some embodiments, two samples of different hydrocarbon concentration are used. In some other embodiments, more than two samples of different hydrocarbon concentration are used.

Thus, step (i) of the method of the first aspect preferably comprises subjecting the samples to IR radiation spanning almost the entire IR region of the electromagnetic spectrum (i.e. at least 450 $cm^{-1}$ to 7800 $cm^{-1}$). However, in certain circumstances it may only be necessary to subject the samples to IR radiation in either the mid infrared (MIR) (i.e. at least 450 $cm^{-1}$ to 4000 $cm^{-1}$) or the near infrared spectrum (NIR) (i.e. at least 4000 $cm^{-1}$ to 7800 $cm^{-1}$). Further, in some instances steps (ii) to (iv) may be conducted on a region of the NIR and/or MIR, in these circumstances it may be more economical and/or practical to subject samples to IR radiation at or around this region. Thus, it may be preferred to subject the samples to IR radiation in a region of the NIR and/or MIR.

Preferably, steps (ii) and/or (vi) of the method (i.e. the IR detection steps) comprise detecting an IR signal in a region of the IR spectrum in which an alkyl signal is known to be located, for example, regions in which —$CH_2$ or —$CH_3$ characteristic peaks, their reflection peaks, their deformational peaks and/or their overtone peaks, are known to be located. Such regions, preferably, comprise about 2930 $cm^{-1}$, about 2870 $cm^{-1}$, about 2850 $cm^{-1}$, about 2830 $cm^{-1}$, about 4250 $cm^{-1}$, about 4300 $cm^{-1}$, about 4330 $cm^{-1}$, about 4350 $cm^{-1}$, about 5690 $cm^{-1}$ and/or about 5800 $cm^{-1}$ (i.e. —$CH_2$ signals) and/or about 2690 $cm^{-1}$, about 2730 $cm^{-1}$, about 2950 $cm^{-1}$, about 4160 $cm^{-1}$, about 4385 $cm^{-1}$, about 5870 $cm^{-1}$ and/or about 5890 $cm^{-1}$ (i.e. —$CH_3$ signals).

As would be appreciated by persons skilled in the art, an IR signal is typically detected across a region of the IR spectrum, as some variation in the exact location of the known peaks would be expected depending upon, for example, the IR spectrometry equipment used and/or variation in the physical characteristics of the sample submitted for analysis. Indeed, it is appreciated by persons skilled in the art that many IR spectrometers may show some instability between scans of the same sample and nonetheless provide adequate stability for performing petroleum hydrocarbon analysis. Further, persons skilled in the art will recognise that some variation in the exact location of a reported peak will often be observed upon the repetition of IR analyses.

The preferred region of the IR spectrum may be expanded to include several alkyl peaks, in particular, regions in which an ethyl signal (i.e. —$CH_2$ signals) and a methyl signal (i.e. —$CH_3$ signal) are known to be located. Thus, preferred regions may be selected from one or more of the group consisting of about 2930 $cm^{-1}$, about 2830 $cm^{-1}$, about 2850 $cm^{-1}$, about 2870 $cm^{-1}$, about 4250 $cm^{-1}$, about 4300 $cm^{-1}$, about 4330 $cm^{-1}$, about 4350 $cm^{-1}$, about 5690 $cm^{-1}$ and about 5800 $cm^{-1}$, and selected from at least one of about 2690 $cm^{-1}$, about 2730 $cm^{-1}$, about 2950 $cm^{-1}$, about 4160 $cm^{-1}$, about 4385 $cm^{-1}$, about 5870 $cm^{-1}$ or about 5890 $cm^{-1}$. In particular, the IR PLS model may utilise —$CH_2$ IR spectra that comprise data in the range of about 2845 $cm^{-1}$ to about 2935 $cm^{-1}$, their overtone peaks in the range of about 4150 $cm^{-1}$ to about 4170 $cm^{-1}$, the range of about 4245 $cm^{-1}$ to about 4355 $cm^{-1}$ and/or the range of about 5680 $cm^{-1}$ to about 5810 $cm^{-1}$, in combination with —$CH_3$ IR spectra that comprise data in the range of about 2685 $cm^{-1}$ to about 2735 $cm^{-1}$, the range of about 2945 $cm^{-1}$ to about 2955 $cm^{-1}$ and/or their overtone peaks in the range of about 4150 $cm^{-1}$ to 4170 $cm^{-1}$, the range of about 4375 $cm^{-1}$ to about 4395 $cm^{-1}$, the range of about 5860 $cm^{-1}$ to about 5880 $cm^{-1}$ and/or the range of about 8580 $cm^{-1}$ to about 8600 $cm^{-1}$.

Thus, in some embodiments, step (i) and step (v) comprise subjecting the sample to IR radiation spanning a region consisting of one or more of: about 1380 $cm^{-1}$, about 2690 $cm^{-1}$, about 2730 $cm^{-1}$, about 2830 $cm^{-1}$, about 2850 $cm^{-1}$, about 2870 $cm^{-1}$, about 2930 $cm^{-1}$, about 2950 $cm^{-1}$, about 4160 $cm^{-1}$, about 4164 $cm^{-1}$, about 4250 $cm^{-1}$, about 4256 $cm^{-1}$, about 4300 $cm^{-1}$, about 4330 $cm^{-1}$, about 4350 $cm^{-1}$, about 4385 $cm^{-1}$, about 5690 $cm^{-1}$, about 5800 $cm^{-1}$, about 5870 $cm^{-1}$ and/or about 5890 $cm^{-1}$.

The detection of multiple alkyl signals in the IR region may provide a more robust model for the prediction of petroleum hydrocarbon concentration in the unknown sample. For example, the predictive model may utilise a region of the IR spectra that detects —$CH_2$ and —$CH_3$ signals. For instance, steps (ii) and/or (vi) of the method of the first aspect may comprise detecting an IR signal in a region comprising the range of about 2730 $cm^{-1}$ to about 2850 $cm^{-1}$, about 2930 $cm^{-1}$ to about 2950 $cm^{-1}$, about 4160 $cm^{-1}$ to about 4250 $cm^{-1}$, about 4350 $cm^{-1}$ to about 4385 $cm^{-1}$, and/or about 5800 $cm^{-1}$ to about 5870 $cm^{-1}$.

However, steps (ii) and/or (vi) may also comprise detecting an IR signal in a region in which a single alkyl signal is known to be located. Preferably, such regions comprise wavenumbers in which a TPH sensitive signal is known to be located. For instance, a region may include a wavenumber of about 2690 $cm^{-1}$, about 2730 $cm^{-1}$ and/or about 4160 $cm^{-1}$. Petroleum hydrocarbon compounds consistently generate a characteristic IR signal at or near 2730 $cm^{-1}$, 2690 $cm^{-1}$ and/or 4160 $cm^{-1}$, particularly at or near 2730 $cm^{-1}$. These TPH sensitive signals appear to avoid any substantial overlap with IR signals generated from mineral components or other naturally-occurring materials commonly found in environmental samples, such as soil samples. In certain circumstances, for instance in the generation of models based on a small sample sizes, the use of these regions of the IR spectrum may remove confounding data giving improved predictive models. For instance, carbonate (—$CO_3$) peaks detectable in the 2600 $cm^{-1}$ to 2500 $cm^{-1}$ range and alkyl (—$CH_3$) peaks detectable in the 2900 $cm^{-1}$ to 2800 $cm^{-1}$ range do not overlap with the TPH sensitive signal at or near 2730 $cm^{-1}$, which may give a low error predictive model of petroleum hydrocarbon concentration, where the sample sizes available would otherwise have been too small to generate a robust model using other regions of the IR spectrum.

Methods for producing a training data set are well known to persons skilled in the art and may be readily available to persons through the use of software applications and/or may involve the manual selection of parameters to optimise the accuracy of models based on the data set. For instance, methods may comprise the selection of spectral ranges, number of factors and/or spectral pre-processing parameters that may improve baseline fit. Further, methods for producing a training data set may comprise the cross-validation of the training data set. Step (iii) preferably comprises using a multivariate chemometric technique such as artificial neural networks, vector support machines, machine learning. Most preferably, step (iii) comprises performing a partial least squares (PLS) analysis. As will be appreciated by persons skilled in the art, multivariate analysis may provide a more robust predictive model than other forms of analysis, such as univariate analysis.

Preferably, steps (iii) and (iv) of the method comprise applying a PLS analysis to the IR signals and generating a PLS predictive model for petroleum hydrocarbon concentration from IR signals comprising a portion of the NIR and/or a portion of the MIR. Preferably, suitable portions of the NIR include regions comprising 4000 $cm^{-1}$ to 4600 $cm^{-1}$, 4000 $cm^{-1}$ to 4800 $cm^{-1}$, 4300 $cm^{-1}$ to 4560 $cm^{-1}$, 5150 $cm^{-1}$ to 5250 $cm^{-1}$ and/or 5700 $cm^{-1}$ to 5900 $cm^{-1}$. Suitable portions of the MIR include regions comprising 2680 $cm^{-1}$ to 2740 $cm^{-1}$, 2820 $cm^{-1}$ to 2940 $cm^{-1}$, 2850 $cm^{-1}$ to 2950 $cm^{-1}$, 2850 $cm^{-1}$ to 2975 $cm^{-1}$ and/or 2800 $cm^{-1}$ to 2950 $cm^{-1}$. In some embodiments, combinations of IR signals and/or regions may be used to generate the predictive model. For example, the predictive model may be generated using an IR signal in the MIR in combination of a signal in the NIR.

As would be appreciated by persons skilled in the art, a suitable range and region of the IR spectrum may be selected depending upon external factors such as the physical heterogeneity of samples, the ability to undertake pre-processing of the sample (e.g. chemical extraction or grinding of the samples), the sample size, water content and any other irregular physical parameter present in the sample soils. For instance, when generating a PLS predictive model using samples comprising large amounts of NOM, the IR regions selected for detection may include the —$CH_3$ signal at about 2730 $cm^{-1}$, about 2690 $cm^{-1}$ and/or about 4160 $cm^{-1}$; these signals exclude many of the —$CH_2$ signals (i.e. the 2845 $cm^{-1}$ to 2935 $cm^{-1}$, the 4150 $cm^{-1}$ to 4170 $cm^{-1}$, the 4245 $cm^{-1}$ to 4355 $cm^{-1}$ and the 5680 $cm^{-1}$ to 5810 $cm^{-1}$ regions) which may bias the model. In some embodiments, the —$CH_3$ signal at about 2730 $cm^{-1}$ is used to predict the concentration of TPH in the presence of NOM. Advantageously, we have found that the signal at about 2730 $cm^{-1}$ allows for the discrimination of TPH in the presence of relatively longer chain NOM material. The signal at 2730 $cm^{-1}$ may be used with one or more other IR signals as previously described.

Preferably, the step of generating a predictive model for hydrocarbon concentration based on the training data set (i.e. step (iv)) comprises:

(a) separately subjecting one or more further samples of known hydrocarbon concentration to infrared (IR) radiation;

(b) separately detecting an IR signal from the further samples; and (c) calibrating the predictive model using the IR signal of the further samples.

Step (c) (i.e. the calibration step) may comprise combining the IR signal(s) of the further sample(s) with the IR signal(s) of the two or more samples of step (i) to (ii) and repeating steps (iii) to (iv) for the combination of IR signals to generate a calibrated predictive model for hydrocarbon. The calibrated model then may be used in future applications of the method of the first aspect, wherein the calibrated model is used in place of steps (i) to (iv) for the future analysis of unknown samples. Each additional calibration step will generate a more robust model which should provide a lower error of prediction.

Any number of further samples may be suitable for inclusion in steps (a) to (c). As would be appreciated by persons skilled in the art, calibrations based upon a small number of samples must show some physical similarity with the unknown samples to avoid generating biases in the predictive model. However, as the number of further samples for calibration increases, differences in the physical characteristics of the further samples with respect to the unknown sample may also increase. Predictive models calibrated on a large number of diverse further samples are expected to be quite robust, and therefore may be more broadly applicable to a variety of unknown sample types. Indeed, it is expected that calibrations performed on a very high number of further samples may generate a universally applicable predictive model.

In a second aspect, the present invention provides a method for generating a model to selectively predict hydrocarbon concentration in a sample of unknown hydrocarbon concentration (the unknown sample), said method comprising the steps of:

(i) separately subjecting two or more samples of known hydrocarbon concentration to infrared (IR) radiation, at least two of the samples having different hydrocarbon concentrations;

(ii) separately detecting an IR signal from the samples of known hydrocarbon concentration;

(iii) analysing the IR signals using a multivariate chemometric technique to produce a training data set;

(iv) generating a predictive model for hydrocarbon concentration based on the training data set;

(v) separately subjecting one or more further sample(s) of known hydrocarbon concentration to infrared (IR) radiation;

(vi) separately detecting an IR signal from the further sample(s) of known hydrocarbon concentration; and thereafter (vii) calibrating the predictive model using the IR signal of the further sample(s) of known hydrocarbon concentration;

wherein application of the predictive model to the unknown sample selectively predicts hydrocarbon concentration therein.

The method of the second aspect preferably provides a method of selectively predicting petroleum hydrocarbon concentration in a sample of unknown petroleum hydrocarbon concentration, wherein step (viii) comprises selectively predicting petroleum hydrocarbon concentration in the unknown sample.

Preferably, step (i) of the method of the second aspect comprises subjecting the sample to IR radiation spanning almost the entire IR region of the electromagnetic spectrum (i.e. at least 450 $cm^{-1}$ to 7800 $cm^{-1}$). However, in certain circumstances it may be practical to subject the sample to IR radiation in either the mid-infrared (MIR) (i.e. at least 450 $cm^{-1}$ to 4000 $cm^{-1}$) or the near-infrared spectrum (NIR) (i.e. at least 4000 $cm^{-1}$ to 7800 $cm^{-1}$) only. For example, where the method utilises portable or relatively basic IR spectroscopy equipment, it may be preferable to subject the sample to mid-infrared (MIR) radiation (i.e. 500 $cm^{-1}$ to 4000 $cm^{-1}$), or near-infrared (NIR) radiation (i.e. 4000 $cm^{-1}$ to 7800 $cm^{-1}$), or optionally a combination of MIR radiation and MR radiation.

To obtain samples of known hydrocarbon concentration, it is envisaged that techniques for determining hydrocarbon concentration known to persons skilled in the art may be applied to unknown samples, for instance GC techniques. More preferably, however, unknown samples may be spiked with known concentrations of hydrocarbon to provide samples of known hydrocarbon concentration. For instance, to generate a predictive model for hydrocarbon concentration in heterogenous or unusual sample types, such as aquifer samples or core samples, a more robust model may be generated by spiking samples of similar composition (e.g. samples from the same site that are known not to contain hydrocarbons) with a known concentration of hydrocarbon.

Step (ii) preferably involves detecting an IR signal in a region of the IR spectrum in which an alkyl signal is known to be located. Preferred regions comprise about 2930 $cm^{-1}$, about 2730 $cm^{-1}$, about 2830 $cm^{-1}$, about 2850 $cm^{-1}$, about 2870 $cm^{-1}$, about 4250 $cm^{-1}$, about 4300 $cm^{-1}$, about 4330 $cm^{-1}$, about 4350 $cm^{-1}$, about 5690 $cm^{-1}$ and/or about 5800 $cm^{-1}$ (i.e. —$CH_2$ signals) and/or about 2690 $cm^{-1}$, about 2730 $cm^{-1}$, about 2950 $cm^{-1}$, about 4160 $cm^{-1}$, about 4385 $cm^{-1}$, about 5870 $cm^{-1}$ and/or about 5890 $cm^{-1}$ (i.e. —$CH_3$ signals).

The methods of the present invention may be performed using standard IR spectroscopy apparatus. For example, for MIR radiation, diffuse reflectance infrared fourier transform spectra (DRIFT) may be measured using a Perkin-Elmer Spectrum-One Fourier transform mid-infrared (FT-MIR) spectrometer (Perkin Elmer Inc, Wellesley, Mass., United States of America). Standard IR spectroscopy apparatus may, however, be modified if desired by the addition of a Pike "Auto-Diff" auto-sampling diffuse reflectance accessory. Further, the scanning methodology utilised in the standard IR spectroscopy apparatus may be optimised for use with the method of the second aspect by, for example, adjusting the scanning duration and resolution (e.g. optimised methods may involve scanning for 60 seconds in the wavenumber range from 4000 cm$^{-1}$ to 500 cm$^{-1}$ (2500 nm to 20000 nm) at a resolution of 8 cm$^{-1}$, followed by repeat scans adjusted for a frequency and/or resolution above and/or below these values). Optimisation of the scanning methodology may also involve carrying out background reference scans, for instance, using silicon carbide (SiC) discs designated with a reflectivity of 1.

These methods may be followed by exporting the spectra directly into Unscrambler™ Ver. 9.80 software (CAMO Technologies Inc, Woodbridge, N.J., United States of America) for chemometrics analysis wherein predictive modelling and calibrating may be carried out (Unscrambler™ Ver. 9.80 software). Options such as the full "leave-one-out" cross-validation (Geladi and Kowalski, 1986) are available with the use of these and similar software applications. PLS regression, and various pre-processing options, such as point to point baseline offset may be used to reduce the effects of non-systematic spectral baseline variance and to capture the most relevant spectral information pertaining to the PLS analysis to develop robust and accurate regression models.

As used herein, cross-validation regression statistics were expressed in terms of the coefficient of determination ($R^2$) and root mean square error of cross-validation (RMSECV). The detection limit is taken to be the RMSECV.

Methods for producing a training data set are well known to persons skilled in the art and may be readily available to persons through the use of software applications and/or may involve the manual selection of parameters to test and optimise the accuracy of models based on the data set. For instance, methods may comprise the selection of spectral range, number of factors and/or pre-processing parameters that may improve baseline fit. Further, methods for producing a training data set may comprise the cross-validation of the training data set. Step (iii) preferably comprises using a multivariate chemometric technique such as PLS, artificial neural networks, vector support machines and/or machine learning. Most preferably, step (iii) comprises performing a partial least squares (PLS) analysis.

Preferably, steps (iii) and (iv) of the method comprise applying a PLS analysis to the IR signals and generating PLS predictive model for petroleum hydrocarbon concentration from IR signals comprising a portion of the NIR and/or a portion of the MIR. Preferably, suitable portions of the NIR include regions comprising 4000 cm$^{-1}$ to 4600 cm$^{-1}$, 4000 cm$^{-1}$ to 4800 cm$^{-1}$, 4300 cm$^{-1}$ to 4560 cm$^{-1}$, 5150 cm$^{-1}$ to 5250 cm$^{-1}$ and/or 5700 cm$^{-1}$ to 5900 cm$^{-1}$. Suitable portions of the MIR include regions comprising 2680 cm$^{-1}$ to 2740 cm$^{-1}$, 2820 cm$^{-1}$ to 2940 cm$^{-1}$, 2850 cm$^{-1}$ to 2950 cm$^{-1}$, 2850 cm$^{-1}$ to 2975 cm$^{-1}$ and/or 2800 cm$^{-1}$ to 2950 cm$^{-1}$.

In performing a selection of suitable regions of the NIR or MIR for steps (iii) and (iv), regard may be had to external factors such as the physical heterogeneity of samples, the ability to undertake pre-processing of the sample (e.g. chemical extraction or grinding of the samples), the sample size, water content and any other irregular physical parameter present in the sample. For instance, for predicting petroleum hydrocarbon samples comprising large amounts of NOM, IR regions that comprise any one of the —$CH_3$ TPH specific signals 2730 cm$^{-1}$, 2690 cm$^{-1}$ and/or 4160 cm$^{-1}$ may be specifically selected as they exclude many of the —$CH_2$ signals (i.e. the 2845 cm$^{-1}$ to 2935 cm$^{-1}$ region, the 4150 cm$^{-1}$ to 4170 cm$^{-1}$ region, the 4245 cm$^{-1}$ to 4355 cm$^{-1}$ region and the 5680 cm$^{-1}$ to 5810 cm$^{-1}$ regions) as these may bias the model. Or, for aqueous or damp samples, regions suited to DRIFT techniques may be specifically selected.

Further, many external physicochemical characteristics of unknown environmental samples may be determined by IR analysis. For instance, the pH, carbonate, particle size (percentage clay, silt, and/or sand), carbon pool concentrations, cation exchange capacity, gravimetric and volumetric water contents, bulk density, and the sorption affinity of the environmental samples to pesticides and other environmental pollutants may be determined by IR methods. Preferably, the methods of the present invention comprise the step of assessing the physical characteristics of samples by IR analysis, more preferably, this step is performed together with generating a predictive model for petroleum hydrocarbon concentration.

The suitability of regions of the NIR or MIR for steps (iii) and (iv) may be determined by performing a cross-validation of the predictive model. Thus, step (iv) may further comprise an internal calibration step performed by cross-validation of the sample data. Cross-validation may provide an indication of the expected error in a prediction provided by the IR predictive model. The results of cross-validation may indicate whether the IR region selected for performing steps (iii) and (iv) is a suitable selection given the sample size, the physical characteristics of the samples, the number of factors utilised in step (iv) and the like. Further, the results of cross-validation will provide the person skilled in the art with the information required to determine whether the model is overfitted. For instance, persons skilled in the art may well appreciate if the sample size is too small and the number of factors too great to provide a low error upon cross-validation. Accordingly, persons skilled in the art may undertake corrective measures, as required, in response to cross-validation results.

Thus, producing a training data set at step (iii) may be made based on the results of cross-validation and step (iii) may be repeated incorporating appropriate adjustments, such as changing the number of factors or region of the IR spectrum, prior to undertaking steps (v) to (vii).

Preferably, step (vii) (i.e. the calibration step) comprises combining the IR signal(s) of the further sample(s) with the IR signal(s) of the two or more samples of step (i) to (ii) and repeating steps (iii) to (iv) for the combination of IR signals to generate a calibrated predictive model for hydrocarbon concentration. The calibrated model then may be used in future applications of the method of the first aspect, wherein the calibrated model is used in place of steps (i) to (iv) for the future analysis of unknown samples.

Alternatively, the calibrated model may be used in place of steps (i) to (iv) in methods of the second aspect for further future calibration of the model. Each additional calibration step may generate a more robust model which should provide a lower error of prediction.

While the methods of the present invention may be suitable for providing a quantitative prediction of hydrocarbon concentration in an unknown sample, they may also be suitable for providing a semi-quantitative assessment of hydrocarbon concentration in an unknown sample, in particular for petroleum hydrocarbon. For example, the method may be operated so as to provide an indication of the absence of petroleum hydrocarbon concentration below a significant threshold point. That is, the methods may be operated to provide an assessment of whether a sample includes petroleum hydrocarbon at a level above or below a regulatory limit (e.g. 10,000 mg/kg petroleum hydrocarbon). The assessment may be achieved using, for example, software to aid in the automation of petroleum hydrocarbon determination (e.g. to perform a calculation of whether a sample includes petroleum hydrocarbon at a level above or below a significant threshold point). In certain circumstances, the predictive models described herein may be adapted to perform a semi-quantitative assessment of petroleum hydrocarbon which may provide a greater accuracy of prediction. Further, limits for semi-quantitative methods may be set to account for expected error in the model (i.e. a pre-determined $R^2$ value), such that a predetermined limit may be biased to obtain false positive results to provide greater accuracy for negative predictions.

In the treatment of petroleum hydrocarbon contaminated soils, existing techniques that are used to monitor the progress of treatment (such as GC techniques) require that samples be taken off-site and prepared, usually by time consuming and lengthy solvent extraction processes, prior to analysis. Further, analyses must be performed on a representative number of samples of the site. The process of monitoring petroleum hydrocarbon treatment efforts can be a time consuming and expensive process with delays in either treatment or testing, in turn, causing costly delays in site redevelopment or re-use.

Thus, the methods of the present invention may be used to intermittently or continuously monitor hydrocarbon concentration and/or other analytes on a site, optionally, in near real time. For instance, on a contaminated soil site the predictive methods may be performed by hardware that is continually scanning a desired region of the IR spectrum. An IR prediction is automated and performed on the constant feed to provide real time predictions of changes of site characteristics, which may include changes in hydrocarbon characteristics and/or other analytes. For instance, such changes may occur as a consequence of remediation efforts or from the continued leaking of contaminants from a point source of contamination. Alternatively, a near real time reading may be determined at various time points to ascertain any change in hydrocarbon concentration and/or other analytes from a first time point to a second time point.

In addition, techniques such as GC analysis do not differentiate between NOM content, which is normally present at a concentration of <5% in soils and sediments (Rayment & Higginson, 1992), from total petroleum hydrocarbon content. Therefore, it is probable that many previous false positive results have resulted in unnecessary petroleum hydrocarbon treatment measures being conducted whilst delaying site redevelopment.

Further, false positive results may be observed in the detection of NOM from interference by TPH in measured samples. Thus, the present methods for quantitation of hydrocarbon in a sample may be used to improve current IR methods for the detection of NOM in samples, particularly for NOM analysis in agricultural applications. The present methods may be used to reduce or eliminate interference from current methods which fail to distinguish between TPH and NOM, or they may be combined with known NOM analyses, such as known IR analyses, to more accurately predict NOM content in a sample.

The methods described herein may find application in the characterisation of the spatial heterogeneity of a site. For instance, for the prediction of petroleum tank leakage, particularly, where tanks may be stored underground and wherein leakage detection presents a practical difficulty. Further applications may include the prediction of petroleum hydrocarbon concentration in dredge materials and other mixed wastes, such as industrial wastes.

In particular, in sites where petroleum hydrocarbons are dispersed from a point source (for instance, in a contamination event such as a petroleum spill) the methods of the present invention may be used alone or together with two or three dimensional spatial mapping methods to determine the location of the petroleum hydrocarbon source and/or to predict the concentration of the petroleum hydrocarbon at the source. Such techniques may be especially advantageous in applications such as oil or petroleum exploration, to determine the location of new reservoirs and the amount of oil contained therein. Spatial maps may be generated using software known to persons skilled in the art (e.g. Surfer distributed by Jandel Inc) and may be selected according to preferences of persons skilled in the art, for instance on the ability of software algorithms to "smooth" or "fill in" missing data.

The methods may, further, find particular advantage in oil or petroleum exploration as detritus is a common source of NOM frequently found in substantial amounts in the vicinity of oil or petroleum reservoirs. The presence of detritic films on the surface of core samples, taken for the purpose of oil or petroleum exploration, pose significant difficulties in the specific detection of petroleum hydrocarbon by conventional techniques, such as GC techniques. Thus, the present methods may provide for the rapid and/or specific selective prediction of hydrocarbon (e.g. NOM and/or TPH) for the characterisation of a core sample, wherein the point source may also be identified.

Further, the methods described herein may be adapted to provide for the temporal characterisation of a site. In instances where the degradation of certain hydrocarbons may have occurred over time, the relationship between concentration of recalcitrant compounds and other hydrocarbon compounds may provide information on the site history. The methods described herein may, therefore, be adapted to characterise TPHs to provide specific site historical information.

Thus, in the present methods, the sample may be a core sample. Methods for extracting core samples from environmental matrices such as soil, sediment, silt or rock in terrestrial or aquatic environments, are well known in the art. The core sample may be directly subjected to IR radiation, for instance an IR beam may scan the entire length or circumference of the exterior surface of a core sample, or an IR beam may scan one or more specific sections of the core sample. For instance, a scan may be taken at 10 cm intervals along the length of the core sample.

Alternatively, the core sample or a portion thereof may be subjected to crushing or grinding. Crushed or ground samples may, optionally, be sieved. The core sample or a portion thereof may be pre-processed to comprise particles measuring less than 500 more preferably, less than 200 µm, and most preferably, less than about 63 µm.

As the physical characteristics of core samples are highly variable from site to site, a predictive model may be generated by utilising spiked unknown core samples with known amounts of hydrocarbon. These spiked samples may be utilised as the two or more samples of known hydrocarbon concentration.

Therefore, in a method of generating a predictive model for hydrocarbon concentration in a core sample, step (i) of the method may comprise:
(a) adding a known amount of hydrocarbon to two or more unknown core samples to provide two or more samples of known hydrocarbon concentration; and
(b) subjecting the two or more samples of known hydrocarbon concentration to infrared (IR) radiation.

The present methods may therefore be used for identifying the location of oil or petroleum hydrocarbon reservoirs and/or characterising the oil or petroleum reservoirs of a known location.

The present methods may be integrated into a detection apparatus specifically adapted for the detection of petroleum hydrocarbon in environmental matrices. That is, the detection apparatus may be a handheld device suitable for performing hydrocarbon predictions in-situ, i.e. without the need to remove the sample from the site, or alternatively, it may be a portable device suitable for the ex-situ prediction of petroleum hydrocarbon on-site, for instance in a mobile laboratory. Said detection apparatus may be adapted for on-site applications by miniaturisation and/or stabilisation of the spectrometer. This may be achieved, for example, by limiting the source of IR radiation in a detection apparatus to the transmission of IR radiation in a limited range, for example, it may be limited to the MIR or NIR or a part thereof.

Further, a detection apparatus adapted for the prediction of hydrocarbon concentration in environmental matrices may comprise software and hardware required to perform an analysis of the IR signal and to make a determination as to the amount of hydrocarbon within predetermined confidence limits. The analysis may, optionally, comprise the software and hardware required to perform a quantitative or semi-quantitative analysis. This may be used to determine whether the sample exceeds a predetermined threshold limit, for example for petroleum hydrocarbon concentration in soils the threshold may be set at a regulatory limit (e.g. 10,000 ppm TPH) to indicate whether the sample falls above or below the acceptable limit.

In a third aspect, the present invention provides a software program for selectively predicting hydrocarbon concentration from inputted IR signal data of an unknown sample, wherein said program performs a calculation comprising:

(i) generating a predictive model for hydrocarbon concentration by applying a multivariate chemometric technique to inputted IR signal data from two or more samples of known hydrocarbon concentration wherein at least two of the samples have different hydrocarbon concentrations to produce a training data set, and calibrating the predictive model using inputted IR signal data of one or more further sample(s) of known hydrocarbon concentration; and thereafter (ii) applying the predictive model to the inputted IR signal data of the unknown sample to provide a selective prediction of hydrocarbon concentration.

It is envisaged that the software of the third aspect may comprise further calculations which automate the performance of the additional steps of the methods of the invention.

The software program of the third aspect may be integrated into a detection apparatus specifically adapted for the detection of petroleum hydrocarbon in environmental matrices. Said software program may be adapted to perform an analysis of the IR signal(s) and to make a determination as to the amount of petroleum hydrocarbon within an unknown sample and within predetermined confidence limits.

The present invention is hereinafter further described by way of the following non-limiting examples and accompanying figures.

EXAMPLES

Materials and Methods

Reference Soil Minerals

Sand (K140), bentonite (STX-1), kaolinite (Ballclay), illite (Tumut) and limestone (calcium carbonate-Univar) were sourced from an in-house minerals collection for the following hydrocarbon sorption analyses. The reference soil minerals were characterised by Rayment and Higginson, (1992) as shown in Table 1.

TABLE 1

Reference soil minerals characterised by standard methods (Rayment and Higginson, 1992)

| Clay type | Clay Name | Particle Density g/cm3 | Total C % | CaCO3 % | Inorg C % | Org C % | Total N % |
|---|---|---|---|---|---|---|---|
| Kaolinte | Ballclay | 2.72 | 0.14 | 0.26 | 0.03 | 0.11 | 0.06 |
| Illite | Tumut | 2.83 | 0.07 | 0.17 | 0.02 | 0.05 | 0.01 |
| Smectite | STX-1 | 2.65 | 0.02 | 0.24 | 0.03 | −0.01 | 0.01 |
| Quartz | K140 Sand | 2.63 | 0.01 | 0.00 | 0.00 | 0.01 | <0.005 |

| | Exchangeable cations (pH 7) | | | | | | | Total CEC determined with NH4 | | |
|---|---|---|---|---|---|---|---|---|---|---|
| Clay type | Ca (cmol+/kg) | Mg (cmol+/kg) | Na (cmol+/kg) | K (cmol+/kg) | Total (cmol+/kg) | ECaP (Ca/SumI) | ESP (Na/Sum) | (NH4) (cmol+/kg) | ECaP (Ca/Total) | ESP (Na/Total) |
| Kaolinte | 16.9 | 1.2 | 0.1 | 0.2 | 18.5 | 0.92 | 0.01 | 15.0 | 1.13 | 0.01 |
| Illite | 9.3 | 1.1 | 0.1 | 0.6 | 11.2 | 0.84 | 0.01 | 11.5 | 0.81 | 0.01 |
| Smectite | 50.2 | 16.8 | 7.5 | 0.2 | 74.6 | 0.67 | 0.10 | 72.6 | 0.69 | 0.10 |
| Quartz | | | | | | | | | | |

| | Exchangeable cations (pH 8.5) | | | | | | | Total CEC determined with NH4 | | |
|---|---|---|---|---|---|---|---|---|---|---|
| Clay type | Ca (cmol+/kg) | Mg (cmol+/kg) | Na (cmol+/kg) | K (cmol+/kg) | Total (cmol+/kg) | ECaP (Ca/SumI) | ESP (Na/Sum) | (NH4) (cmol+/kg) | ECaP (Ca/Total) | ESP (Na/Total) |
| Kaolinte | 14.0 | 0.9 | 0.1 | 0.2 | 15.2 | 0.92 | 0.01 | 14.9 | 0.94 | 0.01 |
| Illite | 9.2 | 1.0 | 0.2 | 0.8 | 11.1 | 0.83 | 0.01 | 12.4 | 0.74 | 0.01 |
| Smectite | 50.3 | 15.0 | 7.1 | 0.3 | 72.5 | 0.69 | 0.10 | 85.6 | 0.59 | 0.08 |
| Quartz | | | | | | | | | | |

Particle Size Separation

Sand was dry sieved to 1000 μm-600 μm, 600 μm-500 μm, 500 μm-300 μm, 300 μm-212 μm, 212 μm-106 μm and 106 μm-63 μm to study the effects of particle size.

Petroleum Hydrocarbon Stock Solutions

Two stock solutions of petroleum hydrocarbons were prepared from crude oil (Light crude blend, BP oil refinery, Kwinana, WA, Australia) and diesel (Navy diesel, BP oil refinery, Kwinana) dissolved in cyclohexane (Merck). For sand sorption studies, a 10% stock solution of crude oil and diesel were prepared from 10 mL petroleum hydrocarbons in cyclohexane to give a total volume of 100 mL. A more dilute stock solution of 2.5% petroleum hydrocarbons in cyclohexane to a total volume of 100 mL was used for sorption experiments with clays. Diluted aliquots of the petroleum hydrocarbons stock solution (0 to 100%) were prepared from 0.00 mL, 0.05 mL, 0.10 mL, 0.25 mL, 0.50 mL, 1.00 mL, 2.00 mL, 2.50 mL, 5.00 mL, 7.50 mL, 10.00 mL and 20.00 mL of petroleum hydrocarbons stock in cyclohexane to give a 10 mL total volume of each aliquot.

Preparation of Mock Contaminated Soils

Aliquots of diesel and crude oil were mixed with fixed weights of each test soil, 10 g for sand and the sandy Ref B soil and 2.5 g for the clays and the high-clay Ref A soil. These were mixed in a tumbler for 12 hrs to ensure an even dispersion of petroleum hydrocarbons throughout the sample particles, and allowed to dry for 18 hr at 40° C. to remove all traces of the cyclohexane solvent. Final concentrations of crude oil (in ppm) are shown in Table 2. Samples were sent to a National Australian Testing Authority (NATA) accredited petroleum laboratory for confirmatory analysis the laboratory spiked samples. A spiked sample concentration of 10,000 ppm gave a confirmatory lab result of 8,140 ppm.

TABLE 2

Concentration of diesel in reference minerals comprising sand, smectite, kaolinite, illite and carbonate

| Sample/spectra name | Tube # | Tube name | Sample treatment (diesel or crude) | matrix | Stock (mL) | Hexane (mL) | Conc of stock soln (mL TPH/mL total) | Conc TPH in sample (V/W %) | sample wt (g) | PPM |
|---|---|---|---|---|---|---|---|---|---|---|
| 1d sand | 1 | 1DS | d | sand | 0.00 | 10.00 | 0.10 | 0.00 | 10.076 | 0 |
| 2d sand | 2 | 2DS | d | sand | 5.000 | 5.000 | 0.000125 | 0.006 | 10.015 | 62 |
| 3d sand | 3 | 3DS | d | sand | 5.000 | 5.000 | 0.000250 | 0.012 | 10.042 | 124 |
| 4d sand | 4 | 4DS | d | sand | 0.05 | 9.95 | 0.10 | 0.05 | 10.009 | 499 |
| 5d sand | 5 | 5DS | d | sand | 0.10 | 9.90 | 0.10 | 0.10 | 10.034 | 996 |
| 6d sand | 6 | 6DS | d | sand | 0.25 | 9.75 | 0.10 | 0.25 | 10.046 | 2482 |
| 7d sand | 7 | 7DS | d | sand | 0.50 | 9.50 | 0.10 | 0.50 | 10.033 | 4959 |
| 8d sand | 8 | 8DS | d | sand | 1.00 | 9.00 | 0.10 | 0.99 | 10.002 | 9899 |
| 9d sand | 9 | 9DS | d | sand | 2.00 | 8.00 | 0.10 | 1.95 | 10.039 | 19533 |
| 10d sand | 10 | 10DS | d | sand | 2.50 | 7.50 | 0.10 | 2.44 | 9.996 | 24400 |
| 11d sand | 11 | 11DS | d | sand | 5.00 | 5.00 | 0.10 | 4.76 | 10.005 | 47596 |
| 12d sand | 12 | 12DS | d | sand | 7.50 | 2.50 | 0.10 | 6.97 | 10.014 | 69677 |
| 13d sand | 13 | 13DS | d | sand | 10.00 | 0.00 | 0.10 | 9.09 | 10.005 | 90868 |
| 1d smec | 1 | 1DSm | d | smec | 0.00 | 10.00 | 0.025 | 0.000 | 2.485 | 0 |
| 2d smec | 2 | 2DSm | d | smec | 1.00 | 9.00 | 0.000125 | 0.005 | 2.502 | 50 |
| 3d smec | 3 | 3DSm | d | smec | 1.00 | 9.00 | 0.000250 | 0.010 | 2.495 | 100 |
| 4d smec | 4 | 4DSm | d | smec | 0.05 | 9.95 | 0.025 | 0.05 | 2.506 | 499 |
| 5d smec | 5 | 5DSm | d | smec | 0.10 | 9.90 | 0.025 | 0.10 | 2.508 | 996 |
| 6d smec | 6 | 6DSm | d | smec | 0.25 | 9.75 | 0.025 | 0.25 | 2.5 | 2494 |
| 7d smec | 7 | 7DSm | d | smec | 0.50 | 9.50 | 0.025 | 0.50 | 2.503 | 4969 |
| 8d smec | 8 | 8DSm | d | smec | 1.00 | 9.00 | 0.025 | 0.99 | 2.502 | 9893 |
| 9d smec | 9 | 9DSm | d | smec | 2.00 | 8.00 | 0.025 | 1.96 | 2.505 | 19569 |
| 10d smec | 10 | 10DSm | d | smec | 2.50 | 7.50 | 0.025 | 2.43 | 2.505 | 24343 |
| 11d smec | 11 | 11DSm | d | smec | 5.00 | 5.00 | 0.025 | 4.80 | 2.481 | 47966 |
| 12d smec | 12 | 12DSm | d | smec | 7.50 | 2.50 | 0.025 | 6.96 | 2.508 | 69560 |
| 13d smec | 13 | 13DSm | d | smec | 10.00 | 0.00 | 0.025 | 9.07 | 2.507 | 90678 |
| 1d kaol | 1 | 1CKa | d | kaol | 0.00 | 10.00 | 0.025 | | | |
| 2d kaol | 2 | 2CKa | d | kaol | 1.00 | 9.00 | 0.000125 | | | |
| 3d kaol | 3 | 3CKa | d | kaol | 1.00 | 9.00 | 0.00025 | | | |
| 4d kaol | 4 | 4CKa | d | kaol | 0.05 | 9.95 | 0.025 | | | |
| 5d kaol | 5 | 5CKa | d | kaol | 0.10 | 9.90 | 0.025 | | | |
| 6d kaol | 6 | 6CKa | d | kaol | 0.25 | 9.75 | 0.025 | | | |
| 7d kaol | 7 | 7CKa | d | kaol | 0.50 | 9.50 | 0.025 | | | |
| 8d kaol | 8 | 8CKa | d | kaol | 1.00 | 9.00 | 0.025 | | | |
| 1d illi | 1 | 1Cil | d | illi | 0.00 | 10.000 | 0.025 | | | |
| 2d illi | 2 | 2Cil | d | illi | 1.000 | 9.000 | 0.000125 | | | |
| 3d illi | 3 | 3Cil | d | illi | 1.000 | 9.00 | 0.00025 | | | |
| 4d illi | 4 | 4Cil | d | illi | 0.05 | 9.95 | 0.025 | | | |
| 5d illi | 5 | 5Cil | d | illi | 0.10 | 9.90 | 0.025 | | | |
| 6d illi | 6 | 6Cil | d | illi | 0.25 | 9.75 | 0.025 | | | |
| 7d illi | 7 | 7Cil | d | illi | 0.50 | 9.50 | 0.025 | | | |
| 8d illi | 8 | 8Cil | d | illi | 1.00 | 9.00 | 0.025 | | | |
| 1d CO3 | 1 | 1D-CO3 | d | CO3 | 0.00 | 10.00 | 0.025 | 0.000 | 2.503 | 0 |
| 2d CO3 | 2 | 2D-CO3 | d | CO3 | 1.00 | 9.00 | 0.000050 | 0.002 | 2.498 | 20 |
| 3d CO3 | 3 | 3D-CO3 | d | CO3 | 1.00 | 9.00 | 0.000100 | 0.004 | 2.512 | 40 |
| 4d CO3 | 4 | 4D-CO3 | d | CO3 | 0.05 | 9.95 | 0.025 | 0.05 | 2.494 | 501 |
| 5d CO3 | 5 | 5D-CO3 | d | CO3 | 0.10 | 9.90 | 0.025 | 0.10 | 2.501 | 999 |
| 6d CO3 | 6 | 6D-CO3 | d | CO3 | 0.25 | 9.75 | 0.025 | 0.25 | 2.498 | 2496 |
| 7d CO3 | 7 | 7D-CO3 | d | CO3 | 0.50 | 9.50 | 0.025 | 0.50 | 2.497 | 4981 |
| 8d CO3 | 8 | 8D-CO3 | d | CO3 | 1.00 | 9.00 | 0.025 | 0.99 | 2.511 | 9858 |
| 9d CO3 | 9 | 9D-CO3 | d | CO3 | 2.00 | 8.00 | 0.025 | 1.96 | 2.5 | 19608 |
| 10d CO3 | 10 | 10D-CO3 | d | CO3 | 2.50 | 7.50 | 0.025 | 2.44 | 2.5 | 24390 |
| 11d CO3 | 11 | 11D-CO3 | d | CO3 | 5.00 | 5.00 | 0.025 | 4.76 | 2.501 | 47601 |

TABLE 2-continued

| 12d CO3 | 12 | 12D-CO3 | d | CO3 | 7.50 | 2.50 | 0.025 | 6.97 | 2.504 | 69664 |
| 13d CO3 | 13 | 13D-CO3 | d | CO3 | 10.00 | 0.00 | 0.025 | 9.10 | 2.497 | 91008 |

| | |
|---|---|
| Kaolinite | Ballclay |
| Illite | Tumut |
| Carbonate | Ca-Carbonate from Univar |
| Soil Cungena from Eyre Pen | Eyre Peninsula |
| Soil ACU1 from CSIRO ACU | CSIRO ACU reference soil |
| Crude density = | 0.87 |
| PPM conversion | 1 mg/kg or 1 mg/L = 1 ppm |

TABLE 3

Concentration of crude oil in reference soils Ref A and Ref B

| Sample/spectra name | Tube # | Tube name | Sample treatment (diesel or crude) | matrix | Stock (mL) | Hexane (mL) | Conc of stock soln (mL TPH/mL total) | Conc TPH in sample (V/W %) | sample wt (g) | PPM |
|---|---|---|---|---|---|---|---|---|---|---|
| 1c Soil | 1 | 1C-ACU1 | c | Soil | 0.00 | 10.000 | 0.025 | 0.00 | 2.587 | 0 |
| 2c Soil | 2 | 2C-ACU1 | c | Soil | 2.50 | 9.500 | 0.000250 | 0.025 | 2.498 | 218 |
| 3c Soil | 3 | 3C-ACU1 | c | Soil | 5.00 | 9.000 | 0.000250 | 0.047 | 2.646 | 411 |
| 4c Soil | 4 | 4C-ACU1 | c | Soil | 0.10 | 9.90 | 0.025 | 0.10 | 2.488 | 873 |
| 5c Soil | 5 | 5C-ACU1 | c | Soil | 0.25 | 9.75 | 0.025 | 0.25 | 2.462 | 2203 |
| 6c Soil | 6 | 6C-ACU1 | c | Soil | 0.50 | 9.50 | 0.025 | 0.47 | 2.654 | 4078 |
| 7c Soil | 7 | 7C-ACU1 | c | Soil | 0.70 | 9.30 | 0.025 | 0.67 | 2.581 | 5859 |
| 8c Soil | 8 | 8C-ACU1 | c | Soil | 0.90 | 9.10 | 0.025 | 0.91 | 2.461 | 7882 |
| 9c Soil | 9 | 9C-ACU1 | c | Soil | 1.20 | 8.80 | 0.025 | 1.14 | 2.601 | 9920 |
| 10c Soil | 10 | 10C-ACU1 | c | Soil | 1.50 | 8.50 | 0.025 | 1.45 | 2.545 | 12633 |
| 11c Soil | 11 | 11C-ACU1 | c | Soil | 2.00 | 8.00 | 0.025 | 1.87 | 2.617 | 16310 |
| 12c Soil | 12 | 12C-ACU1 | c | Soil | 2.50 | 7.50 | 0.025 | 2.43 | 2.509 | 21145 |
| 1c Soil | 1 | 1C-Cungena | c | Soil | 0.00 | 10.00 | 0.00375 | 0.00 | 15.113 | 0 |
| 2c Soil | 2 | 2C-Cungena | c | Soil | 1.00 | 9.00 | 0.00375 | 0.025 | 15.265 | 214 |
| 3c Soil | 3 | 3C-Cungena | c | Soil | 2.00 | 8.00 | 0.00375 | 0.049 | 15.251 | 428 |
| 4c Soil | 4 | 4C-Cungena | c | Soil | 5.00 | 5.00 | 0.00375 | 0.12 | 15.125 | 1077 |
| 5c Soil | 5 | 5C-Cungena | c | Soil | 10.00 | 0.00 | 0.00375 | 0.24 | 15.546 | 2094 |
| 6c Soil | 6 | 6C-Cungena | c | Soil | 2.00 | 8.00 | 0.0375 | 0.48 | 15.508 | 4187 |
| 7c Soil | 7 | 7C-Cungena | c | Soil | 3.00 | 7.00 | 0.0375 | 0.72 | 15.51 | 6265 |
| 8c Soil | 8 | 8C-Cungena | c | Soil | 4.00 | 6.00 | 0.0375 | 0.98 | 15.127 | 8542 |
| 9c Soil | 9 | 9C-Cungena | c | Soil | 5.00 | 5.00 | 0.0375 | 1.23 | 15.059 | 10699 |
| 10c Soil | 10 | 10C-Cungena | c | Soil | 6.00 | 4.00 | 0.0375 | 1.43 | 15.493 | 12454 |
| 11c Soil | 11 | 11C-Cungena | c | Soil | 8.00 | 2.00 | 0.0375 | 1.92 | 15.323 | 16706 |
| 12c Soil | 12 | 12C-Cungena | c | Soil | 10.00 | 0.00 | 0.0375 | 2.44 | 15.012 | 21203 |

| | |
|---|---|
| Soil Cungena from Eyre Pen. | Eyre Peninsula |
| Soil ACU1 from CSIRO ACU | CSIRO ACU reference soil |
| Crude density = | 0.87 |
| PPM conversion | 1 mg/kg or 1 mg/L = 1 ppm |
| limit for sensitive sites | 1000 mg/kg (Netherlands 5000 mg/kg dry weight) |

Preparation of Soils from a Contaminated Site

Two sets of soils were obtained to develop a prediction model for predicting the concentration of TPH in neat "real" contaminated soils using IR techniques. The "Site A" set consisted of 34 soils of a wide range of composition and soil types. A second set of 138 "Site B" samples, varying in soil composition and petroleum hydrocarbon concentration, was provided by a NATA accredited laboratory, however, many of the samples contained only a small amount of soil. Approximately 200-300 g of each of the Site A soils was provided for infrared analysis with varying amounts of Site B soil submitted for IR analysis.

TABLE 4

Site A soil petroleum hydrocarbon concentration for carbon lengths ranging from C6 to C36 (TPH concentrations are also shown)

| | C6-C9 (mg/kg) | C10-C14 (mg/kg) | C15-C28 (mg/kg) | C29-C36) (mg/kg) | PAH (total) (mg/kg) | Total TPH (mg/kg) |
|---|---|---|---|---|---|---|
| Min | 2 | 10 | 10 | 10 | 1 | 32 |
| Max | 20 | 1500 | 53000 | 2400 | 80 | 54412 |
| Mean | 3 | 212 | 9306 | 465 | 13 | 9960 |
| SDev | 3 | 399 | 13470 | 544 | 18 | 13894 |
| Skewness | 4.1 | 2.2 | 1.8 | 1.6 | 2.9 | 1.8 |

TABLE 5

Site B soil petroleum hydrocarbon concentration for carbon lengths ranging from C6 to C36 (TPH concentrations are also shown)

| | C6-C9 (mg/kg) | C10-C14 (mg/kg) | C15-C28 (mg/kg) | C29-C36 (mg/kg) | Total TPH (mg/kg) |
|---|---|---|---|---|---|
| Min | 2 | 5 | 8 | 0 | 1010 |
| Max | 5300 | 8398 | 34028 | 22710 | 58578 |
| Mean | 138 | 1042 | 3165 | 980 | 5286 |

TABLE 5-continued

Site B soil petroleum hydrocarbon concentration for carbon lengths
ranging from C6 to C36 (TPH concentrations are also shown)

| | C6-C9 (mg/kg) | C10-C14 (mg/kg) | C15-C28 (mg/kg) | C29-C36) (mg/kg) | Total TPH (mg/kg) |
|---|---|---|---|---|---|
| SDev | 530 | 1454 | 4484 | 2465 | 7195 |
| Skewness | 7.6 | 2.3 | 3.7 | 6.2 | 4.3 |

A summary of the petroleum hydrocarbon concentration in the Site A and Site B samples is shown in Tables 2 and 3, and the distribution of TPHs is illustrated in the FIGS. 1(a) and (b) histograms. Further, Tables 4 and 5 confirm the identity of TPHs found in the Site A soils and Site B soils, showing that in both soils, most of the TPH was found in the C15 to C28 carbon length fraction.

Trial Site Remediation

A trial was conducted to test the accuracy of the IR PLS model in predicting TPH concentrations in test samples from a petroleum contaminated site, and in predicting the spread of TPH contamination from a point source. The "Farm A" site is a farm which had been contaminated by a leaking diesel tank. Fourteen surface soil samples were collected at 10 cm intervals of increasing distance from the tank. The Farm A samples were scanned by FTIR as received, and again at each stage after air-drying, grinding and heating to 40° C.

Spectroscopy (i) Mid-Infrared (MIR) Spectroscopy

MIR diffuse reflectance spectra were scanned using a Perkin-Elmer Spectrum-One Fourier transform mid-infrared (FT-MIR) spectrometer (Perkin Elmer Inc) on approximately 100 mg of soil. Spectra were scanned for 60 sec in the frequency (wavenumber) range 7800 cm$^{-1}$ to 450 cm$^{-1}$ (wavelength range 1280 nm-22000 nm) at a resolution of 8 cm$^{-1}$, with the near-infrared (NIR) region from 7800 cm$^{-1}$-4000 cm$^{-1}$ (1280 nm-2500 nm) and the MIR region from 4000 cm$^{-1}$ to 500 cm$^{-1}$ (2500 nm to 20000 nm). The spectrometer was equipped with an extended range KBr beam-splitter, a high intensity ceramic source, a deuterium triglycine-sulphate (DTGS) Peltier-cooled detector and a Pike "Auto-Diff" auto-sampling diffuse reflectance accessory. Spectra were expressed in absorbance (A) units (where A=Log Reflectance$^{-1}$). Background reference scans were carried out using silicon carbide (SiC) discs—assumed to have a reflectivity of 1 (100%). Reference scans of crude oil and diesel were carried out by two reflectance methods; as films deposited onto a mirror surface (transflectance) and also as applied to the surface of powdered KBr (DRIFT).

(ii) Near-Infrared (NIR) Dispersive Spectroscopy

Spectra were scanned using a FOSS NIRSystems 6500 Vis-NIR spectrometer (Foss NIRSystems, Silver Springs, Md., United States of America) consisting of a monochromator with a wavelength range of 400 nm-2500 nm and 2 nm intervals. Samples were placed "as received" into a quartz macro-sampling cuvette with an area of approximately 200 nm×25 mm and scanned in reflectance mode. Spectra were then converted into absorbance (A) units. Reference scans of crude oil and diesel were carried out by transmittance using a 1 mm quartz cuvette.

Chemometric Analysis

The full range of spectra was exported into Unscrambler™ Ver. 9.80 software (CAMO Technologies Inc, Woodbridge, N.J., United States of America) for chemometrics analysis. Principal components analysis (PCA) and Partial least squares (PLS) calibrations were carried out with the Unscrambler™ Ver. 9.80 software using full "leave-one-out" cross-validation (Geladi and Kowalski, 1986). PLS regression, and various pre-processing options, such as point to point baseline offset, were used to reduce the effects of non-systematic spectral baseline variance. This pre-processing captured the most relevant spectral information pertaining to the PLS analysis to develop robust and accurate regression models. Cross-validation regression statistics were expressed in terms of the coefficient of determination ($R^2$) and root mean square error of cross-validation (RMSECV). The detection limit was taken as the RMSECV.

Example 1

Spectra of Soil Minerals and Crude Oil

Results and Discussion

Spectra of Soil Minerals

Quartz (as sand) and kaolinite clays give particularly strong MIR spectral signatures near 1100-1000 cm$^{-1}$ (Si—O stretching vibration) and 3690-3620 cm$^{-1}$ (clay lattice Al—OH vibrations) respectively (Van der Marel and Beutelspacher, 1976; Janik et al., 1998; Reeves et al., 1999; and McCarty et al., 2002). Naturally-occurring organic matter (NOM), identified by spectral peaks due to alkyl —CH$_2$ at 2930-2850 cm$^{-1}$, protein amide —OC—NH near 1680 cm$^{-1}$ and 1530 cm$^{-1}$, carboxylate anion COO— at 1600 cm$^{-1}$ and 1400 cm$^{-1}$, and carboxylic acid —COOH near 1720 cm$^{-1}$ (Van der Marel and Beutelspacher, 1976; McCarty et al., 2002) can cause very strong interference with petroleum hydrocarbon alkyl peaks.

Figure 2:
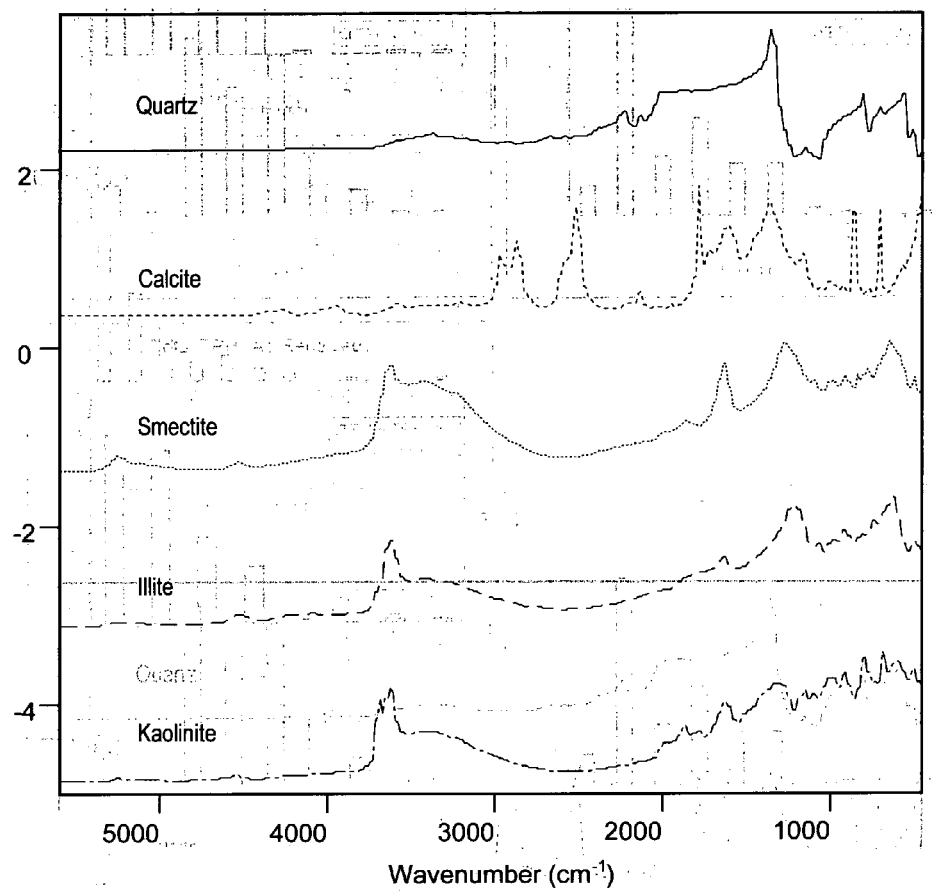
FIG. 2 shows the spectra of reference soil minerals, representing the most common soil minerals, by FT-IR spectroscopy. Arbitrary absorbance units are indicated on the y-axis and wavenumber indicated on the x-axis.

Soils and sediments generally comprise the mineral components of quartz (sand), kaolinite (non-hydrated 1:1 layer alumino-silicate clay), illite (potassium rich 2:1 layer alumino-silicate clays similar to mica) and smectite (hydrated 2:1 layer alumino-silicate clays with high cation exchange capacity). The spectra of these common minerals are shown in FIG. 2. Notably, peaks near 3600 cm$^{-1}$ are associated with Al—OH vibrations in clays such as smectite, illite and kaolinite, along with water absorbed into the clay structures showing broad peaks in the region 3500 cm$^{-1}$-3300 cm$^{-1}$. Quartz does not comprise any significant quantities of aluminium so the 3600 cm$^{-1}$ peaks are not observed, however, peaks below 2000 cm$^{-1}$ are apparent due to the silicate (—SiO$_2$) structure. Carbonate has characteristic peaks near 2980 cm$^1$-2870 cm$^{-1}$, 2600 cm$^{-1}$-2500 cm$^{-1}$ and 1810 cm$^{-1}$, with the main —CO$_3$ fundamental peak near 1375 cm$^{-1}$. These carbonate peaks overlap with the region for the detection of alkyl compounds, mainly in the 2900 cm$^{-1}$-2800 cm$^{-1}$ spectral region. Therefore, the presence of carbonates in environmental matrices may partly conceal the detection of peaks that correspond to the alkane types of total petroleum hydrocarbons (TPHs) such as diesel and crude oil.

FTIR Spectrum of Natural Organic Matter

Figure 3:
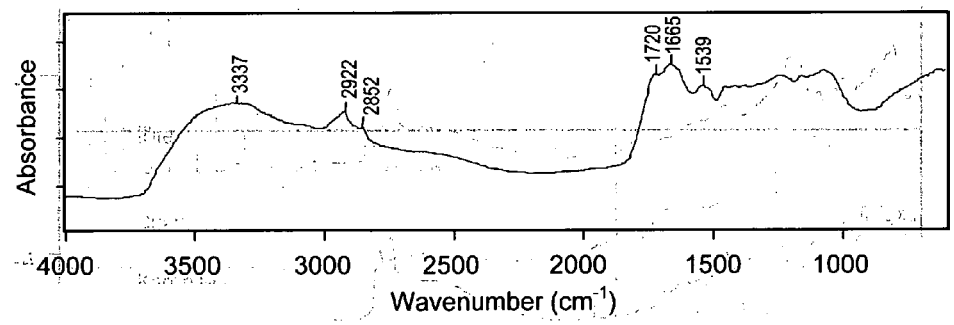
FIG. 3 shows the spectrum of NOM extracted from a reference soil sample.

Natural organic matter (NOM) is known to contribute<5% of the soil mass for Australian soils (Rayment & Higginson, 1992). FIG. 3 shows the spectrum of NOM extracted from soil. The peaks near 2922 cm$^{-1}$ and 2852 cm$^{-1}$ are due to the —CH$_2$ vibrations in alkyl structures from NOM, thought to result from lipids and other components of plant cell wall structures. While TPH compounds also form these alkyl peaks, the peaks predominantly reflect the presence of NOM; that is, there is little contribution to these peaks by —CH$_3$ terminal methyl groups present in TPH compounds.

Spectra of Crude Oil and Diesel

FIG. 3 shows portions of the FT-MIR (2500 cm$^{-1}$-4000 cm$^{-1}$) and FT-NIR (4000 cm$^1$-5000 cm$^{-1}$) spectra of diesel and crude oil in sand. Fundamental alkyl peaks are observed near 2955 cm$^{-1}$ (—CH$_3$), 2931 cm$^{-1}$ and 2856 cm$^{-1}$ (—CH$_2$). These are typical of peaks seen in the MIR for medium chain-length hydrocarbons. Corresponding overtone peaks for these vibrations can be seen in the NIR at 4388 cm$^{-1}$, 4329 cm$^{-1}$ and 4256 cm$^{-1}$. Since medium length alkanes, such as C15 to C28 chain length diesel type of compounds, have a higher proportion of —CH$_3$ than NOM, the relationship between peaks attributed to —CH$_3$ and those attributable to —CH$_3$ may be predictive of TPH even in the presence of NOM.

The Identification of TPH-Sensitive Peaks in the Infrared Spectra for TPH Prediction IR peak frequencies in the MIR at 2950 cm$^{-1}$, 2920 cm$^{-1}$, 2730 cm$^{-1}$ and 1380 cm$^{-1}$, peaks in the NIR and co-variate mineral peaks, particularly for quartz in the 1250 cm$^{-1}$ to 450 cm$^{-1}$ region, were analysed for their suitability for TPH prediction. Two very small peaks were surprisingly and consistently observed near 2730 cm$^{-1}$ and 2690 cm$^{-1}$ in the MIR spectra of diesel and crude oil. It was considered that these peaks, particularly the peak near 2730 cm$^{-1}$, may be due to the first overtone vibration of the —CH$_3$ symmetric deformation mode. The peak at 2730 cm$^{-1}$ may, therefore, be directly related to the TPH content in diesel and crude oil contaminated samples.

DRIFT spectroscopy enabled the enhancement of relatively weak peaks near 7200 cm$^{-1}$, with stronger peaks near 4300 cm$^{-1}$ visible by transmittance or transflectance (data not shown). Peaks due to —CH$_3$ were clearly observed at 4384 cm$^{-1}$, 5867 cm$^{-1}$ and 8387 cm$^{-1}$. Only one peak near 4164 cm$^{-1}$ was considered to be equivalent to the 2730 cm$^{-1}$ peak (i.e. close to the second overtone of the 1370 cm$^{-1}$ —CH$_3$ peak). The methyl —CH$_3$ peaks near 5867 cm$^{-1}$ and at 4384 cm$^{-1}$ were clearly differentiated from the alkyl —CH$_2$ peaks near 5800 cm$^{-1}$ and 5690 cm$^{-1}$ and near 4350 cm$^{-1}$ and 4300 cm$^{-1}$. Therefore, it was considered that these regions may be suitable candidate regions for IR PLS modelling.

Example 2

Reference Soils Ref A and Ref B

Results and Discussion
Spectra of the Reference Soils Spiked with Crude Oil

Spectra of the reference soils, Ref A (high total organic carbon and neutral pH) and Ref B (calcareous sandy soil) are shown in FIG. 4. The Ref A soil is characterised by peaks for kaolinite, organic matter and associated water/hydroxyl groups and quartz (i.e. sand). The Ref B soil is highly calcareous, contains less quartz and some natural organic matter (NOM) and alkyl material, however, the observed alkyl peaks tend to overlap with the carbonate peaks (in the 3000 to 2850 cm$^{-1}$ region). In both soil types, characteristic peaks of common soil components overlap with the main spectral region in which alkane hydrocarbon peaks are expected to be located, i.e. in the main 2900 to 2800 cm$^{-1}$ spectral region.

The reference soils Ref A and Ref B were then spiked according to the concentrations shown in Table 3 resulting in soils with crude oil concentrations in the range of 0-90,000 parts per million (ppm).

a) Ref A Soil

The FT-MIR spectra of Ref A soil samples spiked with 0-90,000 ppm of crude oil are shown in FIG. 5a. The scans show three significant spectral changes with increasing crude oil content; a decrease in the very broad organic matter water peak near 3400 cm$^{-1}$, an increase in the sharp alkyl peaks in the 2950 to 2850 cm$^{-1}$ range, and an increase in the negative quartz —Si—O inversion peak near 1100 to 1200 cm$^{-1}$. These peak changes indicate that crude oil partly displaces water associated with soil organic matter and clay which, in turn, affects the reflection characteristics of the quartz surfaces.

The FT-NIR spectra of the same spiked Ref A soil samples are shown in FIG. 5b. Spectra show a lower absorbance (or higher reflectivity) in the 7000 cm$^{-1}$ region, which corresponds with the expected location of the characteristic clay peak. Still lower absorbance is observed with increasing crude oil presumably due to clay-water interactions and the presence of lattice hydroxyls. However, no change is observed in the —CH region near 4320 cm$^{-1}$, where characteristic NOM peaks are expected to be located.

b) Ref B Soil

Like the Ref A soil, the FT-MIR spectra of the Ref B soil samples spiked with 0-90,000 ppm of crude oil (shown in FIG. 6a) show significant spectral changes with increases in crude oil content. A decrease was observed in the very broad organic matter water peak near 3400 cm$^{-1}$, an increase was observed in the sharp alkyl peaks in the 2950 to 2850 cm$^{-1}$ range (indicated in the inset), and an increase was observed in the negative quartz —Si—O inversion peak near 1100 to 1200 cm$^{-1}$.

In addition, sharp peaks were also observed for carbonate at 2980 cm$^{-1}$ and 2875 cm$^{-1}$, 2600 to 2520 cm$^{-1}$, 1810 cm$^{-1}$ and 1500 cm$^{-1}$. In contrast with the Ref A soils, the Ref B soils show crude oil alkyl peaks at locations that overlap with the expected carbonate overtone peaks at 2980 cm$^{-1}$ and 2875 cm$^{-1}$. The FT-NIR spectra of the spiked Ref B soil samples are shown in FIG. 6b. Like the Ref A soil, the FT-NIR spectra of the spiked Ref B soils show a lower absorbance (higher reflectivity) in the 7000 cm$^{-1}$ region (clay) and lower absorbance due to clay water and lattice hydroxyls with an increase in crude oil. The Ref B soils also show an increase in alkyl peak intensity visually observable in the —CH region at 4320 cm$^{-1}$.

Figure 7:
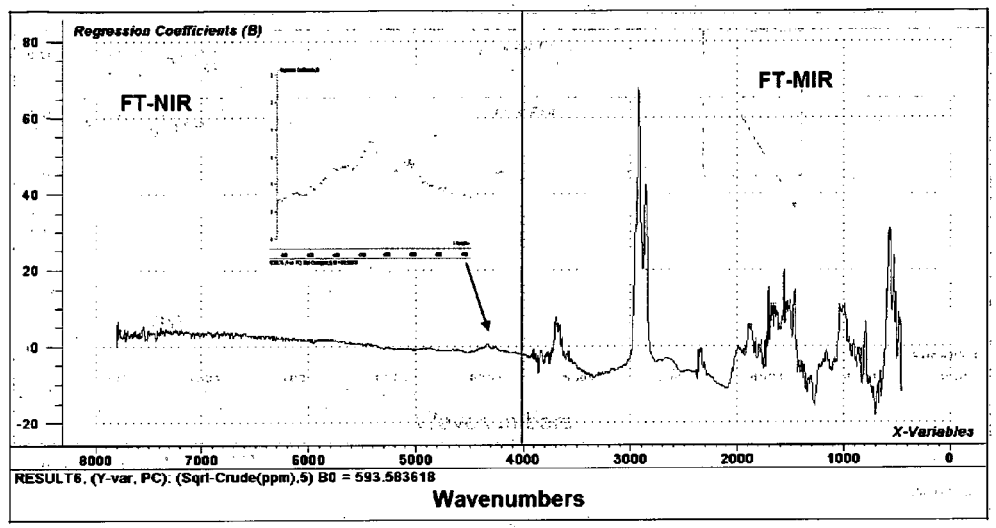
FIG. 7 shows the PLS regression coefficients for five PLS factors with increasing concentrations of crude oil from 0-90,000 ppm sorbed into the Ref A soil. Coefficients in the FT-NIR and FT-MIR spectral regions are shown. The inset highlights the crude oil alkyl peaks in the NIR for crude oil.

PLS Modelling and Cross-Validation of the Reference Soils Spiked with Crude Oil and Diesel a) Ref A soil FT-MIR and FT-NIR scans of the Ref A and the Ref B soils were used to compare the effectiveness of various spectral regions in generating predictive IR PLS models for petroleum hydrocarbon quantitation in soils. PLS regression coefficients are shown in FIG. 7 for five PLS factors (determined by PLS training) with increasing concentrations of crude oil from 0-90,000 ppm sorbed into the Ref A soil, with the inset showing the alkyl peaks in the NIR for crude oil.

Alkyl peaks, due to NOM and crude oil, were observed for the PLS regression coefficients in the MIR at approximately 2930 cm$^{-1}$ and 2950 cm$^{-1}$, respectively, with very small peaks at 4330 cm$^{-1}$ to 4260 cm$^{-1}$ in the NIR. Very small, sharp peaks were seen in the 1450 to 1370 cm$^{-1}$ region and assigned to the —CH$_3$ and —CH$_2$ deformation vibrations, respectively. Peaks in the PLS regression coefficients show the correlation between the spectral intensities and crude oil concentration which corresponds to peaks in the regression loadings. Therefore, the PLS model is confirmed by the expected frequencies for crude oil, which adds confidence to the PLS models.

Table 6 summarises the results of the IR PLS cross-validation for crude oil sorbed onto the Ref A soil; a comparison is shown using different MIR and NIR spectral regions, different TPH concentrations and a different number of factors. The data field shows crude oil concentration at parts per million, the number of samples are shown at N, the coefficient of determination is shown as $R^2$, the root mean square error of cross-validation is indicated at RMSECV, and Range 1, Range2 and Range3 are the three spectral data ranges (cm$^{-1}$ for FTIR and nanometers for the NIRS6500).

TABLE 6

Summary of IR PLS cross-validation regression statistics for FT-MIR, FT-NIR and NIRS6500 spectra of crude oil sorbed onto the reference soils Ref A and Ref B

| Soil | TPH | Data | PLS factors | Range1 | Range2 | Range3 | N | $R^2$ | RMSECV |
|---|---|---|---|---|---|---|---|---|---|
| ACU-1 | Crude | 0-22,000 | 2 | 2975-2850 | | | 12 | 0.89 | 2409 |
| ACU-1 | Crude | 0-10,000 | 2 | 2975-2850 | | | 9 | 0.81 | 1648 |
| ACU-1 | Crude | 0-22,000 | 4 | 4800-4000 | | | 12 | 0.86 | 2706 |
| ACU-1 | Crude | 0-10,000 | 4 | 4800-4000 | | | 9 | 0.58 | 2518 |
| Cungena | Crude | 0-22,000 | 3 | 2942-2820 | | | 12 | 0.86 | 2991 |
| Cungena | Crude | 0-10,000 | 2 | 2942-2856 | | | 6 | 0.99 | 280 |
| Cungena | Crude | 0-22,000 | 3 | 5900-5700 | 5250-5150 | 4600-4000 | 11 | 0.95 | 1654 |
| Cungena | Crude | 0-9,000 | 2 | 4560-4300 | | | 7 | 0.96 | 746 |

FT-MIR with PLS cross-validation of Ref A soil spiked with crude oil achieved an accuracy of $R^2=0.89$ and RMSECV=2,409 ppm for a range of 0-22,000 ppm. There were, however, marked negative prediction errors for the blank soil (0 ppm) of approximately 5,000 ppm, and 5,300 ppm for sample 10 (a nominal concentration of 12,600 ppm) (data not shown). For a narrower range on 0-10,000 ppm, the prediction error RMSECV was 1,674 ppm with an $R^2=0.81$. PLS cross-validation for the Ref A soil in the FT-NIR resulted in higher regression errors, with an $R^2=0.86$ and RMSECV=2,706 ppm with four PLS factors for the full-range 0-22,000 ppm crude oil. The PLS regression coefficients showed peaks in the NIR alkyl region near 4400-4000 $cm^{-1}$. The large number of PLS factors relative to the small number of samples indicates overfitting of the PLS model. Cross-validation for the reduced data range of 0-10,000 ppm was poor, with an $R^2=0.58$ and RMSECV=2,518 ppm for four factors in a spectral range of 4800-4000 $cm^{-1}$. For comparative purposes the RMSECV values may require adjustment as values are dependent on the range of analyte values (so that RMSECV for a 0-100,000 ppm is approximately 10 times larger than for the 0-10,000 ppm range).

b) Ref B Soil

Figure 8:
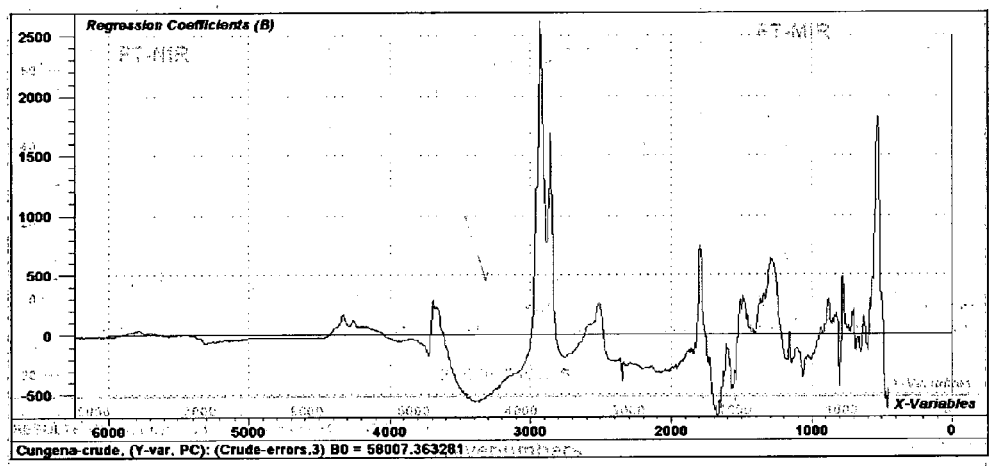
FIG. 8 show the PLS regression coefficients for five PLS factors with increasing concentrations of crude oil from 0-90,000 ppm sorbed into the Ref B soil. Coefficients in the FT-NIR and FT-MIR spectral regions are shown.

FIG. 8 shows the PLS regression coefficients (in the FT-NIR and FT-MIR spectral regions) for five PLS factors with increasing concentrations of crude oil from 0-90,000 ppm sorbed into the Ref B soil. Alkyl peaks are shown at 2930 $cm^{-1}$ and 2950 $cm^{-1}$ and several small NIR peaks are shown at 4330-4260 $cm^{-1}$. Carbonate peaks are observed near 2520 $cm^{-1}$ and 1800 $cm^{-1}$, suggesting a correlation between crude oil sorption and carbonate content.

The Table 6 comparison of the IR PLS cross-validation regression statistic is also shown for crude oil sorbed onto the Ref B soil. FT-MIR with PLS cross-validation of crude oil in the Ref B soil achieved an accuracy of $R^2=0.86$ and RMSECV=2991 ppm for a range of 0-22,000 ppm. For the narrower range of 0-10,000 ppm, the prediction error RMSECV was 280 ppm with an $R^2=0.99$, however, with an analysis of only six samples and two factors there was a risk of overfitting. PLS cross-validation for the Ref B soil in the FT-NIR resulted in lower regression errors with an $R^2=0.95$ and RMSECV=1654 ppm with 3 PLS factors for the full-range 0-22,000 ppm crude oil. PLS regression coefficients showed peaks in three NIR alkyl regions; 59005700 $cm^{-1}$, 5250-5150 $cm^{-1}$ and 4600-4000 $cm^{-1}$. The cross-validation for the reduced data range of 0-9,000 ppm provided a good fit, with an $R^2=0.97$ and RMSECV=746 ppm for two factors and a spectral range of 4560-4300 $cm^{-1}$, however, a risk of overfitting was also present for the NIR in this region.

Conclusions

In general, the anticipated prediction errors in terms of RMSECV and $R^2$ were within acceptable limits for both the 0-22,000 ppm and 0-10,000 ppm concentration ranges of crude oil. For the Ref A soil, a poor regression model was obtained for the FT-NIR region compared with the MIR region, particularly for lower crude oil concentrations. Indeed, the crude oil blank control gave a negative result. In contrast to the Ref A soil, the regression models generated from the Ref B soils are expected to show good predictive ability when modeled on low crude oil concentrations. Surprisingly, the expected difficulties arising from the potential of interference or masking of the TPH alkyl peaks with NOM and carbonate peaks were unrealised, as the PLS regression model was capable of discriminating between data from crude oil, NOM and carbonate.

Example 3

Determination of the Predictive Accuracy of the PLS Model on Farm A

Results and Discussion
Laboratory-Sourced TPH Contaminated Sample Soils
a) Spectra The grinding and air drying soils prior to FTIR-DRIFT scanning was found to be more effective than heating soils to 40° C. and/or scanning unground soils (data not shown). It is suspected that grinding and air drying soils improves sample heterogeneity, since it reduced particle size effects and total reflectance due to water or volatile hydrocarbons in the sample surfaces. Therefore, these pre-treatment steps were undertaken prior to scanning Site A, Site B and Farm A soils.

b) Site A Soils

Figure 9:
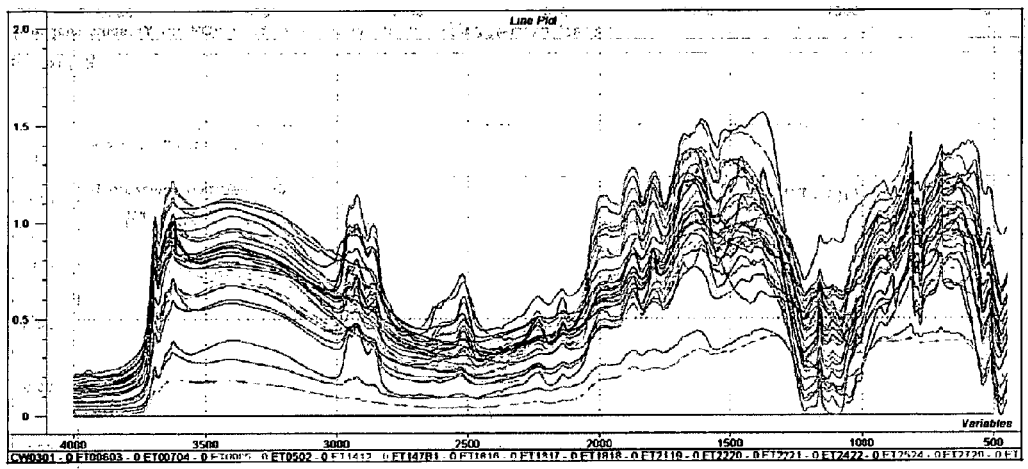
FIG. 9 shows the FTIR spectra of the Site A soils.

The IR spectrum of the Site A soils is shown in FIG. 9, which shows that the soils are, to some extent, fairly similar in mineralogy. All samples contain variable amounts of quartz (sand) and carbonate and sharing similar kaolinite/smectite/illite clay mineralogy. While the amount and type of TPH does vary throughout the sample set, these similarities make this sample set more akin to a site study where the physico-chemical variation in the samples is minimal.

c) Site B Soils

Figure 10:
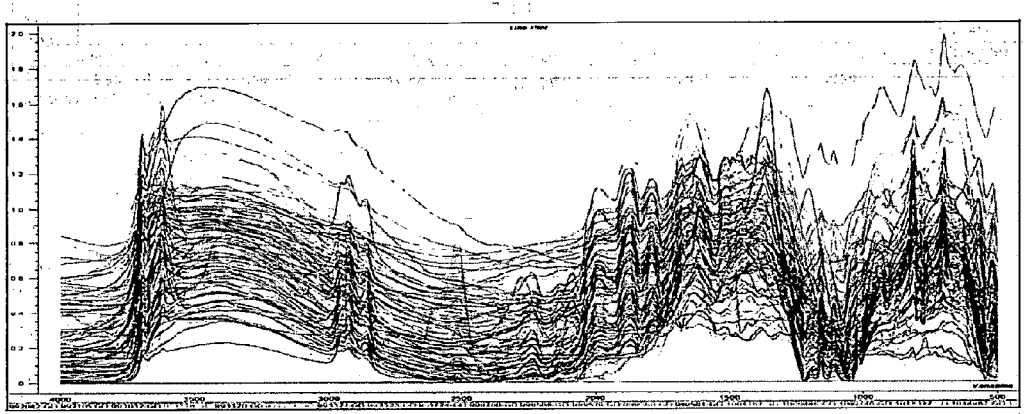
FIG. 10 shows the FTIR spectra of Site B soils.

The FTIR spectra of the ground and dried Site B soils are shown in FIG. 10. FIG. 10 shows significant variation in the spectra between samples, which also ranged from "natural soils" to bright blue synthetic "pastes" indicative of variability in clay mineralogy, amount of quartz, carbonate materials and organic materials (including soil organic matter and hydrocarbons).

IR PLS Cross-Validation a) Site A Soils

Figure 11:
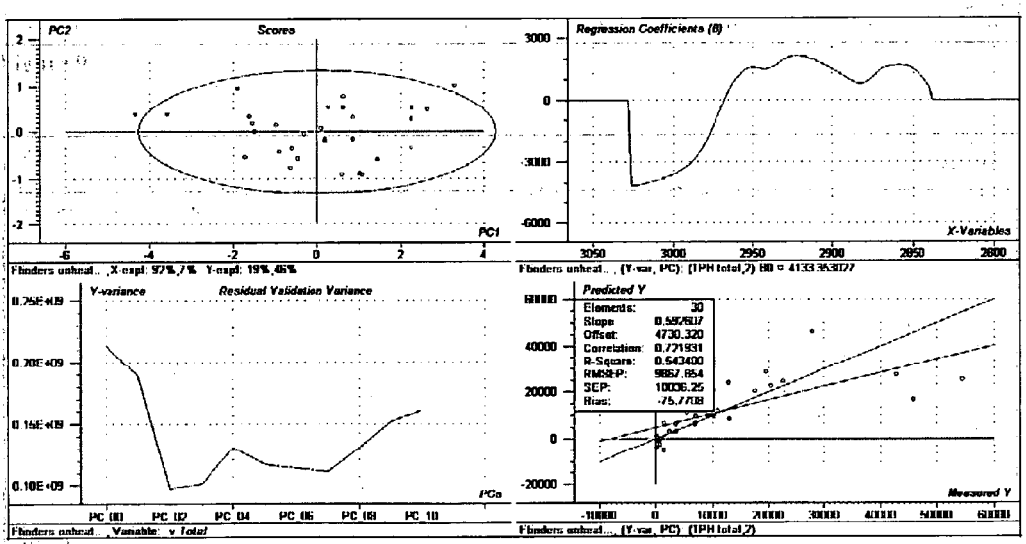
FIG. 11 shows the PLS cross-validation of unground Site A soils, all samples have been included in the PLS statistics.

Results of the cross-validation of the IR PLS model based on the Site A soils data, over the full range of TPH concentrations and focusing on the aliphatic —CH stretch vibration portion of the FT-MIR spectra near 2950 to 2800 cm$^{-1}$, are shown in FIG. 10. The regression analysis anticipated some predictive error showing an $R^2$=0.54 and RMSEP=9867 ppm. To test the model based on a lower TPH concentration range, the three highest TPH samples with concentrations over 20,000 ppm were removed and the IR PLS model based on the lower TPH concentration ranges alone were cross-validated as it was expected that these three samples, which contained a much higher TPH concentration than the rest of the set, would bias the calibration effectively increasing error in the model. The resulting model, shown in FIG. 11, gave an $R^2$=0.82 and an RMSEP=3379 ppm, a result comparable to the laboratory spiked samples and consistent with the required TPH analytical precision threshold for standard methods.

b) Site B Soils

The physical characteristics of the Site B samples were highly varied in nature, therefore some non-soil samples had to be removed. The Site B 138 soil samples were ranked by PCR according to their spectral differences. 24 outlier samples were removed leaving 104 samples for generating the IR PLS model. Two Ref B spiked samples high in crude oil were added to this set to expand the sample size and the TPH range to generate a robust IR PLS model. Initial modeling using the alkyl 2950 to 2850 cm$^{-1}$ spectral region resulted in a very poor PLS model with high expected error, cross-validation giving $R^2$=0.25 and an RMSEP=4930 ppm (data not shown). The poor validation of the regression model may be due to the physical variability (i.e. variability in soil mineralogy and chemistry) in the presented samples, the size of the sub-sample provided (i.e. it may have been too small), or the sub-sample may not have been representative of the whole set that was analysed by the reference laboratory by GC. Spectral effects, such as interference from NOM and carbonate which both give peaks in this region, may also have contributed to the poor validation of the model. Alternative spectral regions, which may be less influenced by these constituents, were investigated for their suitability in generating IR PLS models predictive for TPH.

Figure 12:
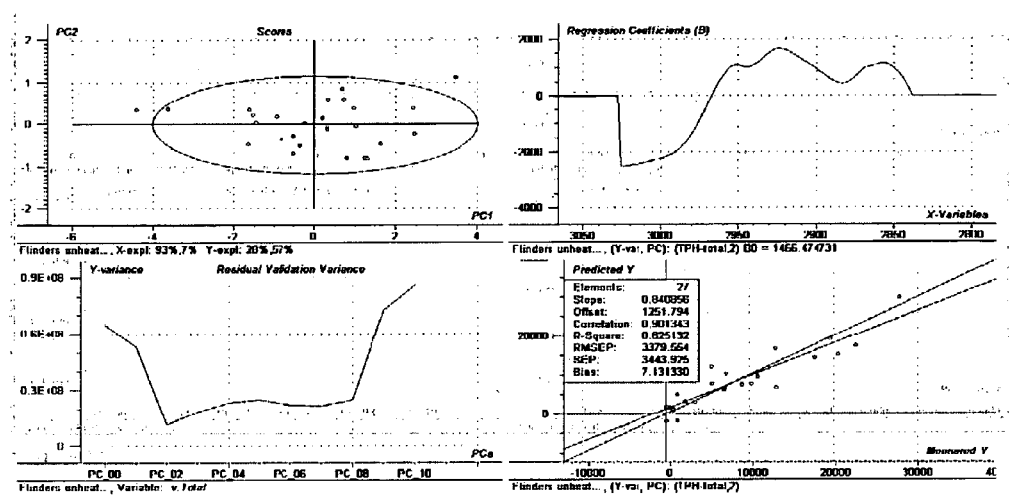
FIG. 12 shows the PLS cross-validation of unground Site A soils, wherein the PLS statistics exclude three samples at a concentration of less that 20,000 ppm of TPH.

A subsequent IR PLS calibration, using a range of the IR spectrum that includes the 2945 cm$^{-1}$ methyl stretching vibration and the small TPH sensitive 2730 cm$^{-1}$ peak (expected to provide a more specific combination of peaks characteristic of TPH) was generated and the results of the cross-validation shown in FIG. 12. The IR PLS model based on the 2800 to 2650 cm$^{-1}$ region and samples of TPH concentration in the range of 0-45,000 ppm showed a much improved IR PLS model, showing an $R^2$=0.56 and an RMSEP=3745 upon cross-validation. While the IR PLS model required more regression factors (approximately seven), error in the model based on the 2800 to 2650 cm$^{-1}$ region was still greater than the model generated from the spiked soils or the Site A set.

Figure 13:
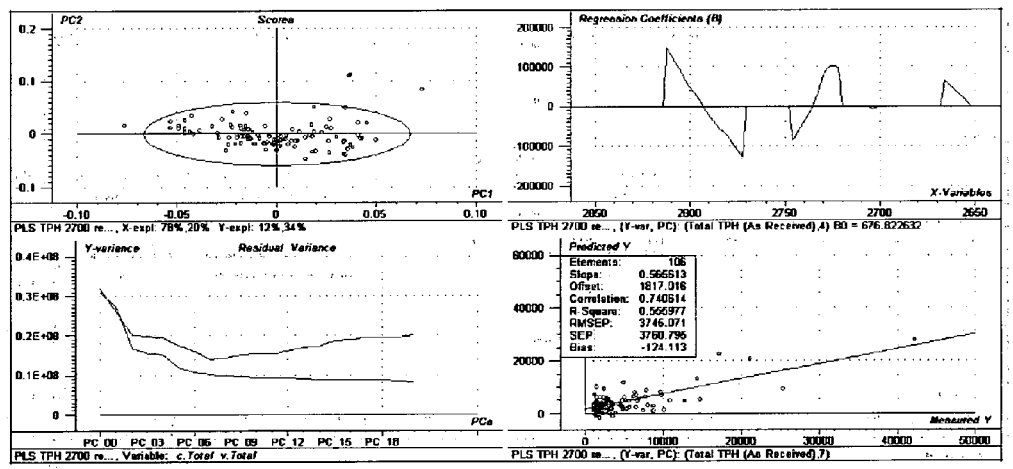
FIG. 13 shows the PLS cross-validation of the Site B soils, wherein the PLS statistics have been performed on reduced spectral regions.

PLS Predictive Ability a) Prediction of TPH in the Site A Soils Using a Combined Ref A-Ref B PLS Calibration As an initial test of the predictive ability of the regression model for TPH in real soils, an IR PLS model was generated based on the combined spiked Ref A and Ref B samples. The model was then used to predict TPH concentration in the Site A sample set. The results of the prediction are shown in FIG. 13, with prediction errors only slightly greater than for the Ref A-Ref B cross-validation. These results suggested that FT-MIR scanning and PLS modeling is a robust predictor of TPHs in contaminated soils. Comparatively, the IR PLS model derived from the NIR portion of the FTIR spectra from the Ref A-Ref B set showed a high modeling error for the FTIR-NIR portion of the spectra.

Test Prediction of Diesel Contamination and Distribution in the Farm A a) The Farm A Spectra A trial of a contaminated site was conducted to test the effectiveness of the IR PLS model to determine the predictive ability of the model and the predictability of the spread of TPH contamination from a point source on a contaminated site. The site, Farm A (in South Australia), contains a leaking diesel tank which acted as a source of contamination of the surrounding soils. 14 soil samples were taken at the soil surface at 10 cm intervals of increasing distance from the tank.

The Farm A samples were scanned by FTIR as received, and were also scanned after air drying, grinding and heating to 40° C. FT-MIR spectra for each of the test treatments, for the sample closest to the contamination source (sample number 13) and the sample furthest from the contamination source (sample number 12) are shown in FIG. 15. The spectra show very little change during the drying and grinding of the sample furthest from the tank, other than for a slight loss of moisture (strong peak at 3400 cm$^{-1}$). In contrast, spectra of the sample closest to the tank (sample number 13) showed significant changes in moisture and diesel intensities following drying and grinding as determined by scanning in the MIR. The strongest reduction in diesel intensity was observed in sample number 13 following grounding and heating treatment (see FIG. 15).

To determine whether the grinding and heating effects observed in sample number 13 would be consistent across samples, spectra of the second closest sample (sample number 14) was compared with the furthest sample (sample number 12) for the various drying and grinding treatments (FIG. 16). Notably, these two samples showed greater physical similarity than sample numbers 12 and 13. A strong increase in the intensity of the water and diesel peaks in the ground sample was observed in the sample 12 spectra (FIG. 16c and FIG. 16d) compared to the untreated sample spectra (FIG. 16a) and the spectra of the dried sample (FIG. 16b). These differences may be due to the breaking up of the soil aggregates, which exposes material including diesel and water from within the particles.

FIG. 17 provides a further insight into the effects of drying and grinding on the spectra of TPH contaminated soils. Intensity of the spectra in FIG. 17a and FIG. 17b are fairly evenly distributed from the closest to the furthest samples, with point 1 being closest to the tank and point 14 being furthest. Apart from point 5 (sample number 3) there was a close agreement in values and trend between predicted and observed values for samples number 2 to sample number 12 (less than 22,000 ppm). While sample number 13 has the highest intensity, sample number 14 is only fourth in order of intensity following sample number 1 and sample number 3. These variations are expected to be caused by the variations in background NOM content as shown by the high proportion of —CH$_2$ (2924 cm$^{-1}$ and 2856 cm$^{-1}$ NOM) compared to —CH$_3$ (2954 cm$^{-1}$ and 2868 cm$^{-1}$ diesel) in sample number 1 and sample number 3. The spectra in FIG. 17c and FIG. 17d further suggest that the sample closest to the leaking tank (sample number 13), with a reference analysis of 180,000 ppm, may contain a significant amount of diesel as surface film. Sample grinding and heating removes this layer and reduces its intensity.

b) PLS Prediction

Total TPH concentration in the Farm A samples was predicted for each of the treatments using an IR PLS model derived from the Site B soils. The model was generated from a widely variable subset of 35 samples, ranging in TPH concentrations of up to 60,000 ppm, with samples selected for modeling on the basis of good PCR fit (FIG. 18). Notably, the spectral region used to generate the IR PLS model included the TPH specific 2730 cm$^{-1}$ peak.

FIG. 18a, which shows the PLS regression coefficients for the first 7 PLS factors in the 2800 to 2600 cm$^{-1}$ spectral region, and FIG. 19b, which shows the FT-MIR PLS calibration for total TPH derived from 35 Site B samples, show that the seven factors IR PLS model achieved the lowest TPH calibration error. However, the R$^2$ value was considered to be too high and the model most likely to be over-fitted, so the IR PLS model was reduced to five factors to provide a more stable calibration (FIG. 19).

FIG. 19a shows the trend of the IR PLS predicted total TPH and laboratory reference values in samples taken along the transect from the source of contamination, with point 1 being closest to the source and point 14 being furthest. Apart from point 5 (sample number 3) there was a close agreement in trend values between predicted and observed values for samples number 2 to number 12 (less than 22,000 ppm).

As demonstrated in FIG. 19b, values predicted by the IR PLS model show close agreement with the reference data, with an R$^2$=0.91. Although the regression slope for the raw predictions was low (slope=0.46), this was increased to close to unity (slope=1.1) after correcting all values for a slope derived from the actual analytical values for sample number 14.

Conclusions

The cross-validation results of the IR PLS model generates from the Site A soils were statistically comparable to the results from the cross-validation of the model generated from spiked samples. The R$^2$=0.82 and RMSECV=3379 ppm values for the final IR-PLS model agrees well with the results obtained from the spiked samples. The poor model generated from the physically and spectrally inconsistent Site B samples was dramatically improved with the removal of non-soil samples and inclusion of two spiked Ref B samples. The Farm A site assessment demonstrated that the predictive ability of the IR PLS model was reasonably accurate for the detection of total TPH in real soils. Samples taken along a regular interval from a point source of contamination showed an excellent agreement in the expected concentration of samples. Good predicted values could even be obtained after suitable slope correction using only one or two laboratory reference values. The IR PLS trend predictions may, therefore, also be used to generate landscape maps of contaminated sites using only a handful of predicted data points and IR PLS predictions and additional two dimensional spatial mapping techniques.

Example 4

In-situ Determination of TPH Contamination

Experimental

Spectra were obtained with a hand-held field portable FTIR instrument in situ at TPH contaminated sites. The soils were collected and sub-sampled for laboratory analysis by GC for TPH and scanning with a bench top FTIR, using diffuse reflectance (DRIFT). Partial least-squares (PLS) cross-validation was used for modelling TPH concentration in the samples, and the development of predictive models for in-field use.

Results and Discussion

Figure 20:
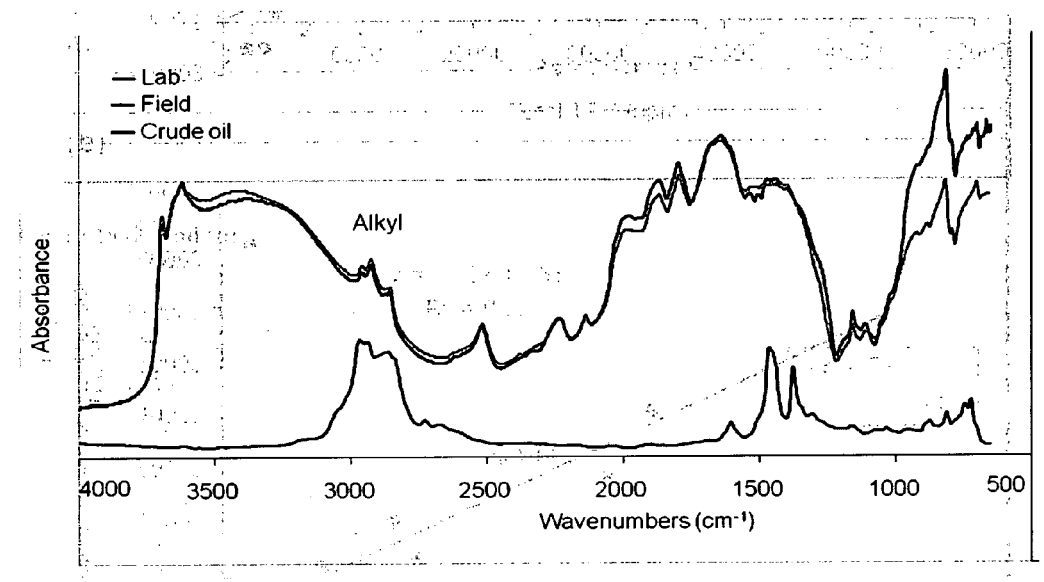
FIG. 20 shows DRIFT mid-infrared spectra of a soil, scanned with a laboratory bench-top and the hand-held field-portable instrument, are shown together with a spectrum of crude oil. The oil shows peaks characteristic of TPH.

The mid-infrared DRIFT spectra of soils from a lab bench-top (1 min. scan) and field-portable instrument (20 sec. scan) are shown in FIG. 20. The spectra were very similar. Hydrocarbon peaks characteristic of alkyl-CH$_3$ and —CH$_2$ stretching vibrations are seen in the 3000-2700 cm$^{-1}$ range.

PLS Regression Analysis

Figure 21:
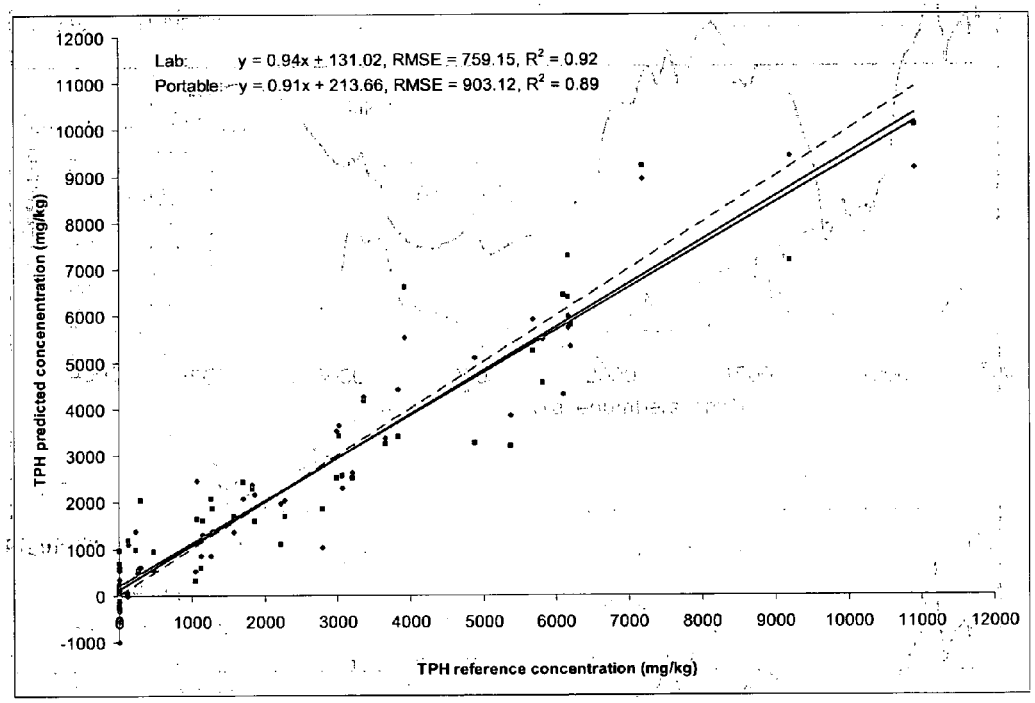
FIG. 21 shows the FT-MIR PLS cross-validation for total TPH in soil samples.

PLS cross-validation for TPH predictions for field soils at contaminated sites are depicted in FIG. 21. Total TPH concentrations ranged from 0-11000 mg/kg giving an RMSECV=759 mg/kg (Lab) and 903 mg/kg (Portable).

Figure 22:
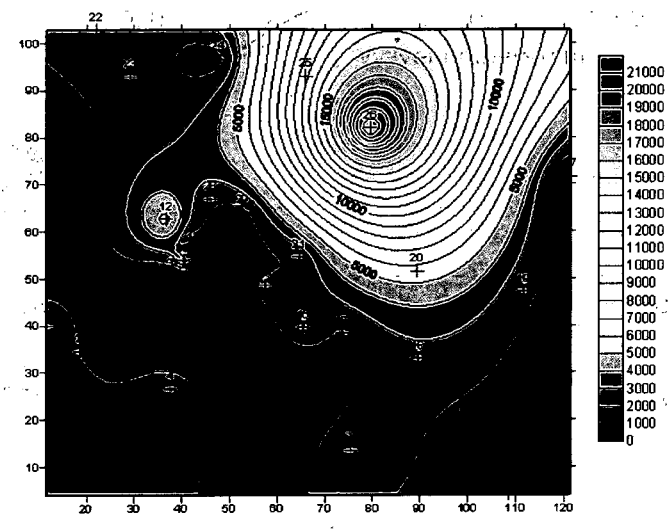
FIG. 22 shows a site survey map of predicted TPH ppm at a contaminated site.

A site survey map of TPH ppm at the contaminated site was then produced (FIG. 22).

Conclusion

DRIFT with PLS regression analysis satisfies the accuracy requirements for rapid screening, provided that the model uses the most effective spectral signatures. The predicted TPH values for in-field screening can also be normalised by reference laboratory control data. This example shows that it is possible to discriminate between TPH and SOM. This study also shows that, with recent availability of truly field portable IR spectrometers, the in situ measurement of petroleum contaminants in soils is possible.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Cozzolino D, Moron A. (2003) The potential of near-infrared reflectance spectroscopy to analyse soil chemical and physical characteristics *Journal of Agricultural Science*. Volume: 140 Pages: 65-71 Part: Part 1.

Geladi, P & Kowalski, B R. Partial least-squares regression: a tutorial. *Analytica Chimica Acta* 185:1-17 (1986).

Janik, L J, Merry, R H & Skjemstad, J O. Can mid infrared diffuse reflectance analysis replace soil extractions? *Aust. J. Exp. Agric.* 38:681-696 (1998).

McCarty G W, Reeves J B, Reeves V B, et al. Mid-infrared and near-infrared diffuse reflectance spectroscopy for soil carbon measurement. Soil Science Society of America Journal 66(2):640-646 (2002).

Rayment, G & Higginson, H. Australian Laboratory Handbook of Soil and Chemical Methods, Australian Soil and Land Survey Handbook, Inkata Press, (1992).

Reeves J B, McCarty G W, & Meisinger J. J. Near infrared reflectance spectroscopy for the analysis of agricultural soils. *Journal of Near Infrared Spectroscopy* 7(3):179-193 (1999).

Sadler, R & Connell, D. Analytical methods for the determination of total petroleum hydrocarbons in soil, *Proceedings of the 5th National Workshop on the Assessment of Site Contamination* Pages 133-150 (2003).

Van der Marel H W & Beutelspacher H. Clay and related minerals. In "Atlas of infrared spectroscopy of clay minerals and their admixtures". (Elsevier Scientific: Amsterdam) (1976).

The invention claimed is:

1. A method of selectively predicting petroleum hydrocarbon concentration in an environmental sample of unknown hydrocarbon concentration (the unknown sample) without extraction of the petroleum hydrocarbon from the environmental sample, said method comprising the steps of:
   (i) separately subjecting two or more samples of known hydrocarbon concentration to infrared (IR) radiation using diffuse reflectance spectroscopy, at least two of the samples having different hydrocarbon concentrations;
   (ii) separately detecting an IR signal from the samples of known hydrocarbon concentration;
   (iii) analysing the IR signals using a multivariate chemometric technique to produce a training data set;
   (iv) generating a predictive model for hydrocarbon concentration based on the training data set;
   (v) subjecting the unknown sample to infrared (IR) radiation using diffuse reflectance spectroscopy;
   (vi) detecting an IR signal from the unknown sample;
   (vii) applying the predictive model to the IR signal from the unknown sample; and thereafter
   (viii) selectively predicting petroleum hydrocarbon concentration in the unknown sample.

2. A method according to claim 1, wherein step (i) and step (v) comprise the crushing, grinding, sieving and/or drying of the samples prior to subjecting the samples to IR radiation.

3. A method according to claim 1, wherein step (i) and step (v) comprise subjecting the sample to IR radiation spanning at least 450 $cm^{-1}$ to 7800 $cm^{-1}$.

4. A method according to claim 1, wherein step (i) comprises subjecting three or more samples of known hydrocarbon concentration to infrared (IR) radiation, wherein each sample of known hydrocarbon concentration has a different concentration.

5. A method according to claim 1, wherein step (viii) comprises selectively predicting petroleum hydrocarbon concentration in the unknown sample.

6. A method according to claim 1, wherein step (i) and step (v) comprise subjecting the sample to IR radiation spanning a region consisting of one or more of: 1380 $cm^{-1} \pm 10$ $cm^{-1}$, 2690 $cm^{-1} \pm 10$ $cm^{-1}$, 2730 $cm^{-1} \pm 10$ $cm^{-1}$, 2830 $cm^{-1} \pm 10$ $cm^{-1}$, 2850 $cm^{-1} \pm 10$ $cm^{-1}$, 2870 $cm^{-1} \pm 10$ $cm^{-1}$, 2930 $cm^{-1} \pm 10$ $cm^{-1}$, 2950 $cm^{-1} \pm 10$ $cm^{-1}$, 4160 $cm^{-1} \pm 10$ $cm^{-1}$, 4164 $cm^{-1} \pm 10$ $cm^{-1}$, 4250 $cm^{-1} \pm 10$ $cm^{-1}$, 4256 $cm^{-1} \pm 10$ $cm^{-1}$, 4300 $cm^{-1} \pm 10$ $cm^{-1}$, 4330 $cm^{-1} \pm 10$ $cm^{-1}$, 4350 $cm^{-1} \pm 10$ $cm^{-1}$, 4385 $cm^{-1} \pm 10$ $cm^{-1}$, 5690 $cm^{-1} \pm 10$ $cm^{-1}$, 5800 $cm^{-1} \pm 10$ $cm^{-1}$, 5870 $cm^{-1}$ and/or 5890 $cm^{-1} \pm 10$ $cm^{-1}$.

7. A method according to claim 6, wherein step (i) and step (v) comprise subjecting the sample to IR radiation of 2730 $cm^{-1} \pm 10$ $cm^{-1}$.

8. A method according to claim 6, wherein step (i) and step (v) comprise subjecting the sample to IR radiation in a combination of two or more regions.

9. A method according to claim 1, wherein the multivariate chemometric technique of step (iii) comprises a partial least squares (PLS) analysis.

10. A method according to claim 1, wherein steps (iii) and step (iv) utilise portions of the IR spectrum comprising 4000 $cm^{-1}$ to 4600 $cm^{-1}$, 4000 $cm^{-1}$ to 4800 $cm^{-1}$, 4300 $cm^{-1}$ to 4560 $cm^{-1}$, 5150 $cm^{-1}$ to 5250 $cm^{-1}$, 5700 $cm^{-1}$ to 5900 $cm^{-1}$, 2680 $cm^{-1}$ to 2730 $cm^{-1}$, 2820 $cm^{-1}$ to 2940 $cm^{-1}$, 2850 $cm^{-1}$ to 2950 $cm^{-1}$, 2850 $cm^{-1}$ to 2975 $cm^{-1}$ and/or 2800 $cm^{-1}$ to 2950 $cm^{-1}$.

11. A method according to claim 1, wherein the step of generating a predictive model for hydrocarbon concentration based on the training data set comprises:
   (a) separately subjecting one or more further sample(s) of known hydrocarbon concentration to infrared (IR) radiation;
   (b) separately detecting an IR signal from the further sample(s); and
   (c) calibrating the predictive model using the IR signal of the further sample(s).

12. A method for generating a model to selectively predict petroleum hydrocarbon concentration in an environmental sample of unknown hydrocarbon concentration (the unknown sample) without extraction of the petroleum hydrocarbon from the environmental sample, said method comprising the steps of:
   (i) separately subjecting two or more samples of known hydrocarbon concentration to infrared (IR) radiation using diffuse reflectance spectroscopy, at least two of the samples having different hydrocarbon concentrations;
   (ii) separately detecting an IR signal from the samples of known hydrocarbon concentration;
   (iii) analysing the IR signals using a multivariate chemometric technique to produce a training data set;
   (iv) generating a predictive model for hydrocarbon concentration based on the training data set;
   (v) separately subjecting one or more further sample(s) of known hydrocarbon concentration to infrared (IR) radiation using diffuse reflectance spectroscopy;
   (vi) separately detecting an IR signal from the further sample(s) of known hydrocarbon concentration; and thereafter
   (vii) calibrating the predictive model using the IR signal of the further sample(s) of known hydrocarbon concentration;
   wherein application of the predictive model to the unknown sample selectively predicts petroleum hydrocarbon concentration therein.

13. A method according to claim 12, wherein the multivariate chemometric technique of step (iii) comprises a partial least square (PLS) analysis.

14. A method according to claim 12, wherein step (iv) comprises an internal calibration step performed by cross-validation of the sample data.

15. A method according to claim 12, wherein step (vii) comprises adding a further sample of known hydrocarbon concentration to the two or more samples of known hydrocarbon concentration of step (i) and repeating steps (i) to (iv) for all of the samples of known hydrocarbon concentration to generate a calibrated predictive model for hydrocarbon concentration.

* * * * *